United States Patent
Kamtekar et al.

(10) Patent No.: US 10,497,875 B2
(45) Date of Patent: Dec. 3, 2019

(54) HOLE TRANSPORTING CYCLOBUTENE COMPOUND

(71) Applicants: Cambridge Display Technology Limited, Godmanchester (GB); Sumitomo Chemical Company Limited, Tokyo (JP)

(72) Inventors: Kiran Kamtekar, Godmanchester (GB); Florence Bourcet, Godmanchester (GB); Tania Zuberi, Godmanchester (GB); Sheena Zuberi, Godmanchester (GB); Thomas Kugler, Cambridge (GB)

(73) Assignees: Cambridge Display Technology Limited, Godmanchester (GB); Sumitomo Chemical Company Limited, Tokyo (JP)

( * ) Notice: Subject to any disclaimer, the term of this patent is extended or adjusted under 35 U.S.C. 154(b) by 37 days.

(21) Appl. No.: 15/325,031

(22) PCT Filed: Jul. 8, 2015

(86) PCT No.: PCT/GB2015/051982
§ 371 (c)(1),
(2) Date: Jan. 9, 2017

(87) PCT Pub. No.: WO2016/005750
PCT Pub. Date: Jan. 14, 2016

(65) Prior Publication Data
US 2017/0207394 A1   Jul. 20, 2017

(30) Foreign Application Priority Data
Jul. 9, 2014   (GB) .................................. 1412238.6

(51) Int. Cl.
*C08G 61/12* (2006.01)
*C07C 13/567* (2006.01)
(Continued)

(52) U.S. Cl.
CPC ........ *H01L 51/0058* (2013.01); *C07C 13/567* (2013.01); *C08G 61/12* (2013.01);
(Continued)

(58) Field of Classification Search
CPC ............................ H01L 51/00; H01L 51/0058
USPC .......................................................... 528/397
See application file for complete search history.

(56) References Cited

FOREIGN PATENT DOCUMENTS

| EP | 2 067 805 A1 | 6/2009 |
|----|----|----|
| GB | 2509718 A | 7/2014 |

(Continued)

OTHER PUBLICATIONS

GB1412238.6, May 19, 2015, Combined Search and Examination Report.

(Continued)

*Primary Examiner* — Duc Truong
(74) *Attorney, Agent, or Firm* — Wolf, Greenfield & Sacks, P.C.

(57) ABSTRACT

A material substituted with a group of formula (I): wherein: $Ar^1$ is an aryl or heteroaryl group; $Sp^1$ represents a first spacer group; n1 is 0 or 1; m1 is 1 if n1 is 0 and m1 is at least 1 if n1 is 1; $R^1$ independently in each occurrence is H or a substituent, with the proviso that at least one R1 is a group R11 selected from: alkyl comprising a tertiary carbon atom directly bound to a carbon atom of the cyclobutene ring of formula (I); branched alkyl wherein a secondary or tertiary carbon atom of the branched alkyl is spaced from a carbon atom of the cyclobutene ring of formula (I) by at least one —$CH_2$— group; and alkyl comprising a cyclic alkyl group; or with the proviso that at least two $R^1$ groups are linked to form a ring.

15 Claims, 6 Drawing Sheets

(51) Int. Cl.
 *H01L 51/00* (2006.01)
 *C09K 11/06* (2006.01)
 *H01L 51/50* (2006.01)
(52) U.S. Cl.
 CPC .......... *C09K 11/06* (2013.01); *H01L 51/0035* (2013.01); *H01L 51/0039* (2013.01); *H01L 51/0043* (2013.01); *C07C 2602/06* (2017.05); *C07C 2603/18* (2017.05); *C08G 2261/124* (2013.01); *C08G 2261/148* (2013.01); *C08G 2261/1412* (2013.01); *C08G 2261/1414* (2013.01); *C08G 2261/18* (2013.01); *C08G 2261/228* (2013.01); *C08G 2261/312* (2013.01); *C08G 2261/314* (2013.01); *C08G 2261/3142* (2013.01); *C08G 2261/3162* (2013.01); *C08G 2261/512* (2013.01); *C08G 2261/95* (2013.01); *H01L 51/0005* (2013.01); *H01L 51/5048* (2013.01); *H01L 51/5056* (2013.01)

(56) References Cited

FOREIGN PATENT DOCUMENTS

| JP | 2009-295974 A | 12/2009 |
|---|---|---|
| JP | 2010-065213 A | 3/2010 |
| JP | 2013-023491 A | 2/2013 |
| JP | 2013-060585 A | 4/2013 |
| WO | WO 2013/005026 A2 | 1/2013 |
| WO | WO 2013/007966 A1 | 1/2013 |

OTHER PUBLICATIONS

PCT/GB2015/051982, Oct. 15, 2015, International Search Report and Written Opinion.
Combined Search and Examination Report dated May 19, 2015 for Application No. GB1412238.6.
International Search Report and Written Opinion dated Oct. 15, 2015 for Application No. PCT/GB2015/051982.
Duerr et al., Benzocyclobutenylidene—Cycloadditions, Reactivity, and Multiplicity. J Org Chem. Mar. 1, 1980;45(6):973-80.
Straub, 1, 2-Di-t.-Butyl-3,4,5,6-Tetramethyl-Benzocyclobutadien. Tetrahedron Lett. Jan. 1, 1976;17(39):3513-4.
[No Author Listed] Welcome to STN International. American Chemical Society. May 30, 2018, 72 pages.
Japanese communication for Application No. JP 2017-500336 dated May 17, 2019.
Matsuya et al., Accelerated Electrocyclic Ring-Opening of Benzocyclobutenes under the Influence of a β-Silicon Atom. Journal of the American Chemical Society. 2006;128(2):412-413.

HOLE TRANSPORTING CYCLOBUTENE COMPOUND

RELATED APPLICATIONS

This application is a national stage filing under 35 U.S.C. § 371 of international PCT application, PCT/GB2015/051982, filed Jul. 8, 2015, which claims priority to United Kingdom patent application, GB 1412238.6, filed Jul. 9, 2014, each of which is incorporated herein by reference in its entirety.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

A hole-transporting layer may be provided between the anode and the light-emitting layer.

US 2012/0256537 discloses a composition comprising a light-emitting or charge-transporting polymer having a crosslinkable group and a light-emitting or charge-transporting low molecular weight compound having a crosslinkable group.

WO 2013/005026 discloses hole-transporting polymers having substituted benzocyclobutene groups. Use of these polymers as the hole-transporting layer of an OLED is disclosed. The substituted benzocyclobutene groups are crosslinked to render the layer insoluble. The benzocyclobutene groups may be reacted with each other or may be reacted with a double bond group.

It is an object of the invention to improve performance of organic electronic devices, in particular organic light-emitting devices, in which one or more layers of the device is formed by deposition of a semiconducting layer of the device by a solution deposition method.

SUMMARY OF THE INVENTION

In a first aspect the invention provides a material substituted with a group of formula (I):

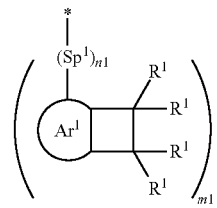

wherein:
$Ar^1$ represents an aryl or heteroaryl group that may be unsubstituted or substituted with one or more substituents;
$Sp^1$ represents a first spacer group;
n1 is 0 or 1;
m1 is 1 if n1 is 0 and m1 is at least 1 if n1 is 1;
$R^1$ independently in each occurrence is H or a substituent, with the proviso that at least one $R^1$ is a group $R^{11}$ selected from:
  alkyl comprising a tertiary carbon atom directly bound to a carbon atom of the cyclobutene ring of formula (I);
  branched alkyl wherein a secondary or tertiary carbon atom of the branched alkyl is spaced from a carbon atom of the cyclobutene ring of formula (I) by at least one —$CH_2$— group; and
  alkyl comprising a cyclic alkyl group;
or
with the proviso that at least two $R^1$ groups are linked to form a ring;
and * represents a point of attachment to the material.

In a second aspect the invention provides a composition comprising a material according to the first aspect and a second material substituted with at least one group of formula (II):

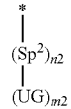

wherein
$Sp^2$ represents a second spacer group;
n2 is 0 or 1;
m2 is 1 if n2 is 0 and m2 is at least 1 if n2 is 1;
UG is a group comprising a reactive unsaturated group; and
* represents a point of attachment to the second material.

In a third aspect the invention provides a method of forming a layer of an organic electronic device comprising the step of reacting a material according to the first aspect or a composition according to the second aspect.

DESCRIPTION OF THE DRAWINGS

The invention will now be described in more detail with reference to the drawings in which.

DETAILED DESCRIPTION OF THE INVENTION

Figure 1:
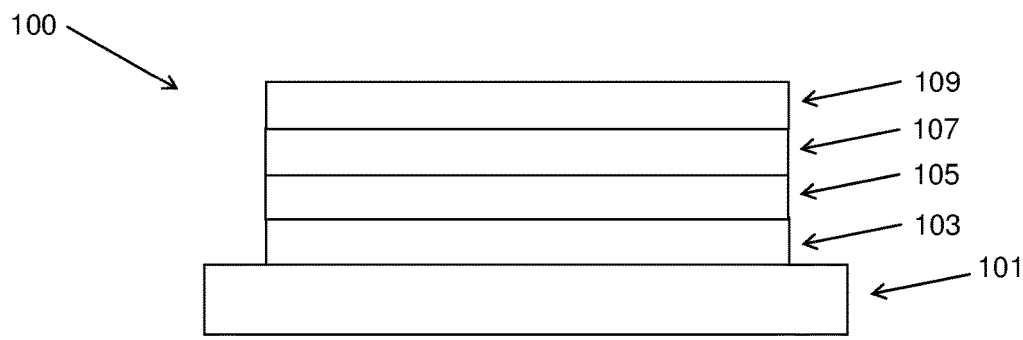
FIG. 1 illustrates schematically an OLED according to an embodiment of the invention.

FIG. 1, which is not drawn to any scale, illustrates an OLED 100 according to an embodiment of the invention comprising an anode 103, a cathode 109, a light-emitting layer 107 between the anode and cathode and a hole-transporting layer 105 between the anode and the light-emitting layer. The device 100 is supported on a substrate 101, for example a glass or plastic substrate.

Light-emitting layer 107 may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display. If the light-emitting layer 107 is patterned then hole-transporting layer 105 may be patterned in the same way as the light-emitting layer, or a patterned light-emitting layer 107 may be formed on an unpatterned hole-transporting layer 105.

Hole-transporting layer 105 contains a hole-transporting material. The hole-transporting layer is formed by reacting a first material containing a group of formula (I).

The first material may be reacted with itself or may be reacted with a second material containing a group of formula (II).

Preferably the first material is reacted with the second material.

The reactive unsaturated group UG may be a reactive double bond or triple bond. Preferably, the reactive double bond or triplet bond of UG is not conjugated.

To form the hole-transporting layer 105, the first material is deposited over the anode. The group of formula (I) is then reacted either with itself or, if present, with groups of formula (II) and light-emitting layer 107 is then formed on the hole-transporting layer 105.

Preferably, the light-emitting layer is formed by depositing a formulation of the material or materials of the light-emitting layer dissolved or dispersed in a solvent or solvent mixture followed by evaporation of the solvent or solvents. Preferably, hole-transporting layer 105 is rendered insoluble by the reaction of the group of formula (I) such that little or none of the hole-transporting layer is dissolved by the solvent or solvents used to form the light-emitting layer, and such that there is little or no intermixing between the materials of the hole-transporting layer and the material or materials of the light-emitting layer. Preferably, the first group of formula (I) reacts, either with itself or with the group of formula (II) of a second material, to form a crosslinked hole-transporting layer.

One or more further layers may be provided between the anode 103 and cathode 109. Further layers may be selected from one or more further light emitting layers, hole-injection layers, hole-transporting layers, electron transporting layers, hole blocking layers and electron blocking layers.

Preferred device structures include:

Anode/Hole transporting layer/Light-emitting layer/Cathode

Anode/Hole-injection layer/Hole-transporting layer/Light-emitting layer/Cathode

Anode/Hole-injection layer/Hole-transporting layer/Light-emitting layer/Electron-transporting layer/Cathode.

Preferably, both a hole injection layer and hole-transporting layer are present.

Light-emitting materials of the OLED 100 may be fluorescent materials, phosphorescent materials or a mixture of fluorescent and phosphorescent materials. Light-emitting materials may be selected from polymeric and non-polymeric light-emitting materials. Exemplary light-emitting polymers are conjugated polymers, for example polyphenylenes and polyfluorenes examples of which are described in Bernius, M. T., Inbasekaran, M., O'Brien, J. and Wu, W., Progress with Light-Emitting Polymers. Adv. Mater., 12: 1737-1750, 2000, the contents of which are incorporated herein by reference. Light-emitting layer 107 may comprise a host material and a fluorescent or phosphorescent light-emitting dopant. Exemplary phosphorescent dopants are row 2 or row 3 transition metal complexes, for example complexes of ruthenium, rhodium, palladium, rhenium, osmium, iridium, platinum or gold.

Light-emitting layer 107 may be the only emissive layer of the device, or light may be emitted from one or more further layers of the device. A light-emitting dopant may be provided in hole-transporting layer 105 such that hole-transporting layer 105 emits light when the device is in use.

The OLED may be a white-emitting OLED. A white-emitting OLED may contain a single, white-emitting layer or may contain two or more layers that emit different colours which, in combination, produce white light. White light may be produced from a combination of red, green and blue light-emitting materials provided in a single light-emitting layer or distributed within two or more light-emitting layers. In a preferred arrangement, the device has a light-emitting layer comprising a red light-emitting material and a light-emitting layer comprising green and blue light-emitting materials.

The light emitted from a white-emitting OLED may have CIE x coordinate equivalent to that emitted by a black body at a temperature in the range of 2500-9000K and a CIE y coordinate within 0.05 or 0.025 of the CIE y co-ordinate of said light emitted by a black body, optionally a CIE x coordinate equivalent to that emitted by a black body at a temperature in the range of 2700-4500K.

A blue light emitting material may have a photoluminescent spectrum with a peak in the range of 420-490 nm, more preferably 420-480 nm.

A green light emitting material may have a photoluminescent spectrum with a peak in the range of more than 490 nm up to 580 nm, optionally more than 490 nm up to 540 nm.

A red light emitting material may optionally have a peak in its photoluminescent spectrum of more than 580 nm up to 630 nm, optionally 585-625 nm.

In another embodiment (not shown) light-emitting layer 107 may be formed by reaction of a group of formula (I) as described herein, either with itself or with a group of formula (II), in which case hole-transporting layer 105 may or may not be present. Light-emitting layer 107 of this embodiment may be the only layer between the anode and the cathode, or one or more further layers, for example as described above, may be provided between the anode and cathode.

In another embodiment (not shown), an electron-transporting layer or electron injecting layer may be provided between the light-emitting layer 107 and the cathode 109 wherein the electron-transporting or electron-injecting layer is formed by crosslinking a first material. The first material may be reacted with itself, or the electron-transporting or electron-injecting layer may be formed by reacting a composition comprising a first material and a second material. The device of this embodiment may contain the light-emitting layer 107 and the electron-transporting or electron-injecting layer only between the anode and cathode, or one or more further layers, for example as described above, may be provided between the anode and cathode.

Formula (I)

Exemplary alkyl groups $R^{11}$ may be selected from $C_{4-20}$ alkyl groups.

In the case where $R^{11}$ contains a tertiary carbon atom directly bound to a carbon atom of the cyclobutene ring of formula (I), $R^{11}$ may be an alkyl containing two or more tertiary carbon atoms.

In the case where $R^{11}$ comprises a cyclic alkyl, $R^{11}$ may consist of a cyclic alkyl group or may be a cyclic alkyl group substituted with one or more $C_{1-5}$ alkyl groups. The cyclic alkyl group may be bound directly to the cyclobutene ring of formula (I) or may be spaced apart therefrom by one or more —$CH_2$— groups, optionally one, two or three —$CH_2$— groups.

In the case where $R^{11}$ comprises a secondary or tertiary carbon atom spaced apart from the cyclobutene ring of formula (I), the secondary or tertiary carbon atom may be spaced from the cyclobutene ring of formula (I) by at least one —$CH_2$— group, optionally one, two or three —$CH_2$— groups. $R^{11}$ comprising a secondary or tertiary carbon atom spaced apart from the cyclobutene ring of formula (I) may contain one, two or more carbon atoms selected from secondary and tertiary carbon atoms.

In the case where two $R^1$ groups are linked to form a ring, the ring may be unsubstituted or substituted with one or more substituents. Exemplary substituents are $C_{1-20}$ alkyl. The ring may be a monocyclic or polycyclic ring. Exemplary rings formed by linkage of two $R^1$ groups are $C_{1-10}$ cycloalkyl groups Exemplary groups $R^{11}$ include the following, wherein * is a point of attachment of the cyclic alkyl group to the cyclobutene ring of the group of formula (I):

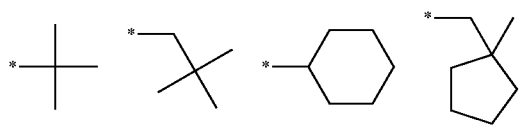

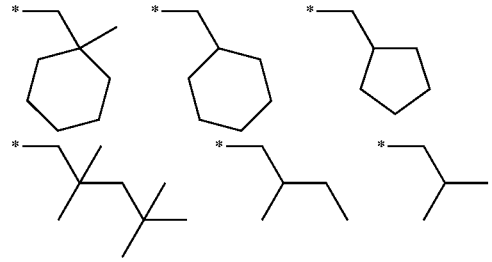

Exemplary structures are illustrated below wherein $R^1$ groups are linked to form a ring. The ring is shown fused to a benzocyclobutyl ($Ar^1$=benzene).

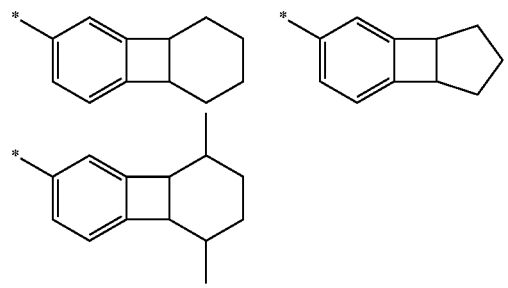

One, two, three or all four groups $R^1$ may be a group $R^{11}$. Optionally, only one group $R^1$ is a group $R^{11}$.

Other groups $R^1$ may be selected from:

H linear $C_{1-20}$ alkyl;

$C_{1-20}$ alkoxy;

tri(hydrocarbyl)silyl;

aryl or heteroaryl that may be unsubstituted or substituted with one or more substituents, optionally phenyl that may be unsubstituted or substituted with one or more $C_{1-10}$ alkyl or $C_{1-10}$ alkoxy groups.

Preferably, 3 $R^1$ groups are H.

$Sp^1$ may be a group of formula —$(R^{12})_t$— wherein t is at least 1, optionally 1, 2, 3, 4 or 5 and each $R^{12}$ is independently selected from the group consisting of:

$C_{1-20}$ alkyl wherein one or more non-adjacent C atoms of the alkyl may be replaced with, O, S, $SiR^{14}_2$ wherein $R^{14}$ in each occurrence is independently a substituent or an aryl or heteroaryl group that may be unsubstituted or substituted with one or more substituents; and aryl or heteroaryl that may be unsubstituted or substituted with one or more substituents.

$Sp^1$ may be substituted with one or more arylcyclobutene groups. $Sp^1$ may be a branched group having at least two branches wherein at least two of the branches are substituted with arylcyclobutene groups.

$R^{14}$ independently in each occurrence may be a hydrocarbyl group, optionally a hydrocarbyl group selected from $C_{1-20}$ alkyl and phenyl that may be unsubstituted or substituted with one or more $C_{1-10}$ alkyl groups.

Aryl or heteroaryl groups $Sp^1$ or forming part of $Sp^1$ are preferably selected from $C_{6-20}$ aryl groups that may be unsubstituted or substituted with one or more substituents, preferably phenyl that may be unsubstituted or substituted with one or more substituents, optionally one or more $C_{1-10}$ alkyl groups.

Exemplary spacer groups $Sp^1$ include $C_{1-20}$ alkyl, $C_{3-20}$ cyclic alkyl, $C_{1-20}$ alkoxy, phenyl, phenyl-$C_{1-20}$ alkyl; phenyl-$C_{1-20}$ alkoxy; groups containing polyether units for example a spacer of formula —$(C_2H_5O)_p$— or -phenyl-$(OC_2H_5)_p$— wherein p is at least 2, optionally 2-10 and phenyl is unsubstituted or substituted with one or more substituents, optionally one or more $C_{1-20}$ alkyl groups; —$(R^{10})_q$—$Si(R^{14})_2$—$(R^{10})_q$— wherein $R^{14}$ is as described above; $R^{10}$ in each occurrence is $C_{1-20}$ hydrocarbyl; and q in each occurrence is 0 or 1. $R^{10}$ in each occurrence may independently be selected from $C_{1-20}$ alkyl and phenyl that may be unsubstituted or substituted with one or more $C_{1-10}$ alkyl groups.

Optionally, $Ar^1$ is an aryl group, optionally a $C_{6-20}$ aryl group, that may be unsubstituted or substituted with one or more substituents.

Preferably, $Ar^1$ is phenyl that may be unsubstituted or substituted with one or more substituents, optionally one or more $C_{1-10}$ alkyl groups.

Formula (II)

$Sp^2$ may independently in each occurrence be selected from groups $Sp^1$ described above.

$Sp^2$ may be substituted with one or more reactive unsaturated groups UG. $Sp^2$ may be a branched group having at least two branches wherein at least two of the branches are substituted with UG groups.

UG may be an acyclic, cyclic or polycyclic group.

An exemplary group of formula (II) having an acyclic group UG has formula (XIa):

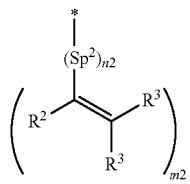

(XIa)

wherein $R^2$ and $R^3$ are each independently H a substituent. Substituents $R^2$ and $R^3$ are optionally selected from $C_{1-20}$ hydrocarbyl, more preferably $C_{1-10}$ alkyl. Preferably, each $R^3$ is H. Preferably, n2 is 1 and m2 is 1.

An exemplary polycyclic group UG is norbornene which may be unsubstituted or substituted. An exemplary group of formula (II) having a norbornene group UG has formula (XIb), wherein the or each norbornene may be unsubstituted or substituent with one or more substituents:

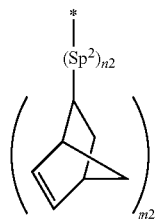

(XIb)

Exemplary substituents of cyclic or polycycic groups UG, for example norbornene, are $C_{1-20}$ alkyl wherein one or more non-adjacent C atoms may be replaced with O, S, S—O, C=O or COO; aromatic groups, optionally phenyl, that may be unsubstituted or substituted with one or more substituents; heteroaromatic groups that may be unsubstituted or substituted with one or more substituents; nitrile; and nitro.

$C_{1-20}$ alkyl groups may be linear, branched or cyclic alkyl groups. Substituents of aromatic or heteroaromatic groups, where present, may be selected from $C_{1-20}$ alkyl.

First and Second Materials

The material substituted with a group of formula (I) may be a non-polymeric material or a polymer comprising a repeat unit substituted with a group of formula (I).

A non-polymeric material may have formula (IIIa):

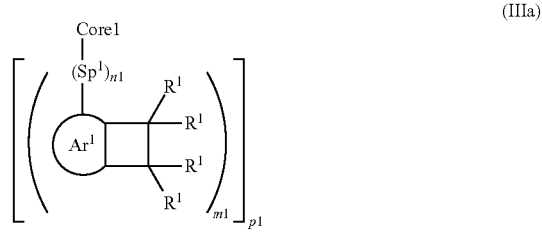

(IIIa)

wherein Core1 is a non-polymeric first core group; $Ar^1$ is an aryl or heteroaryl group that may be unsubstituted or substituted with one or more substituents; $Sp^1$ is a first spacer group; n1 is 0 or 1; if n1 is 0 then m1 is 1; if n1 is 1 then m1 is at least 1, optionally 1, 2 or 3; and p1 is at least 1, optionally 1, 2, 3 or 4.

"Non-polymeric" as used herein means a material having a polydispersity of 1, and includes dendrimeric or oligomeric compounds having a polydispersity of 1. Oligomers include, without limitation, a dimer, a trimer, a tetramer or a pentamer. Preferably, non-polymeric materials have a molecular weight of less than about 5000 Daltons.

A polymer substituted with a group of formula (I) may be a polymer comprising a repeat unit of formula (IIIb):

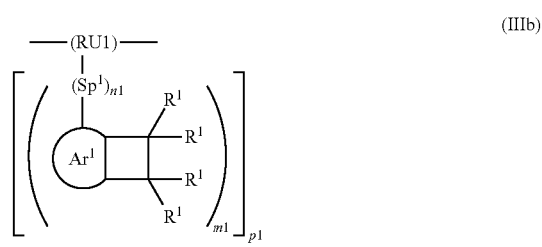

(IIIb)

wherein RU1 is a first repeat unit and p1 is at least 1.

A repeat unit of formula (IIIb) may form 0.5-50 mol % of the repeat units of the polymer, optionally 1-20 mol % of the repeat units.

$Ar^1$ of formula (IIIa) or (IIIb) may be bound Core1 or RU1 respectively, either directly or through $Sp^1$, through any position of $Ar^1$. Preferably, $Ar^1$ is not bound through a ring atom of Ar1 that is adjacent to an atom of the cyclobutene ring.

A non-polymeric second material may have formula (IVa):

(IVa)

wherein Core2 is a non-polymeric second core group; $Sp^2$ is a second spacer group; n2 is 0 or 1; UG is a reactive unsaturated group; if n2 is 0 then m2 is 1; if n2 is 1 then m2 is at least 1, optionally 1, 2 or 3; and p2 is at least 1, optionally 1, 2, 3 or 4.

A polymer substituted with a group of formula (II) may be a polymer comprising a repeat unit of formula (IVb):

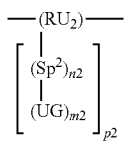
(IVb)

wherein RU2 is a second repeat unit. A repeat unit of formula (IVb) may form 0.5-50 mol % of the repeat units of the polymer, optionally 1-20 mol % of the repeat units.

Repeat units of formula (IIIb) and repeat units of formula (IVb) may be repeat units of the same polymer.

A non-polymeric compound may contain at least one group of formula (I) (p1 is at least 1) and at least one group of formula (II) (p2 is at least 1), for example a compound of formula (XII) wherein Core3 is a non-polymeric third core group that may be selected from any core group described herein with reference to Core1 or Core2:

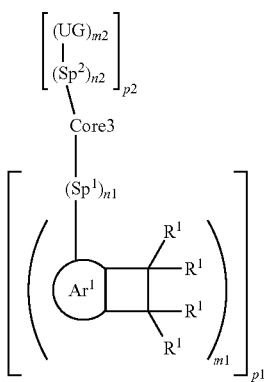
(XII)

In this case, the first material and second material are the same core material to which the group or groups of formula (I) and the group or groups of formula (II) are substituted.

The present inventors have found that groups of formula (I) react more readily that compounds in which the cyclobutene ring is unsubstituted (each $R^1$=H). This may allow groups of formula (I) to react at lower temperature and/or may require shorter reaction time than the case where each $R^1$=H. Furthermore, when reacted with a second material, the present inventors have found that the presence of an $R^{11}$ group or linkage of two $R^1$ groups results in suppression of trimer or higher oligomer formation arising from reactions of groups of formula (I) with each other.

The first material may be reacted with itself or, if present, with the reactive unsaturated group of a second material, by thermal treatment and/or by irradiation, for example UV irradiation. Preferably, the compositions are reacted by thermal treatment. Preferably, thermal treatment is at a temperature of less than 180° C., more preferable less than 160° C. Thermal treatment may be at a temperature of at least 130° C., optionally at least 140° C. Preferably the first and second materials are reacted.

If the first material is a non-polymeric material having only one group of formula (I) (m1 and p1 are each 1) and second material is a non-polymeric having only one group of formula (II) (m2 and p2 are each 1) then these materials may be reacted to give a Diels-Alder adduct as illustrated in Scheme 1 in the case where UG is a norbornene group.

Scheme 1

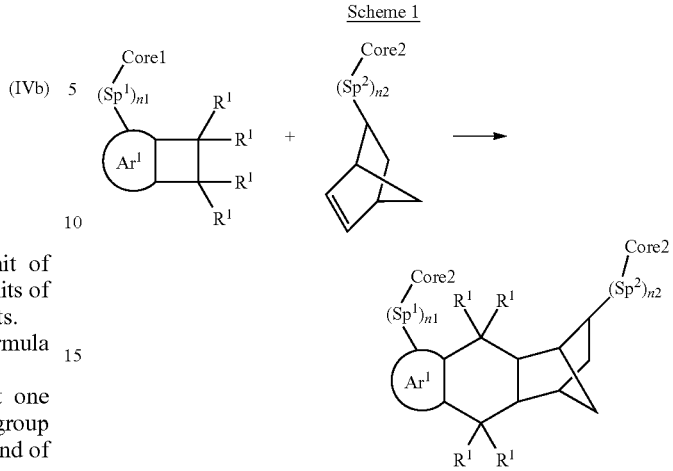

If the first non-polymeric material is substituted with two groups of formula (I), for example if m1=1 and p1=2, and if the second non-polymeric material is substituted with two groups of formula (II), for example if m2=1 and p2=2, then the first and second materials may react to form a linear polymer having the following repeating structure:

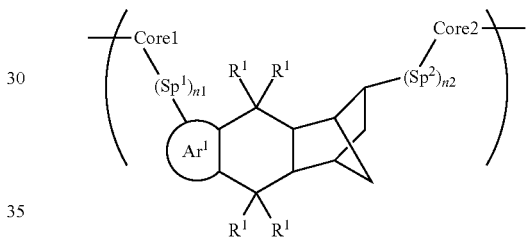

If the first non-polymeric material contains more than two (hetero)arylcyclobutene groups and/or if the second non-polymeric material is substituted with more than two reactive unsaturated groups then the first and second materials may react to form a crosslinked polymer.

If at least one of the first and second materials is a repeat unit of a polymer then the reaction may be a crosslinking reaction.

Scheme 2 illustrates a crosslinking reaction between two chains of a polymer comprising a repeat unit of formula (IVb) wherein UG is norbornene and a non-polymeric compound of formula (IIIa) wherein m1 is 1 and p1 is 2, although it will be appreciated that m1 may be greater than 1 and/or p1 may be greater than 2, for example 3 or 4:

Scheme 2

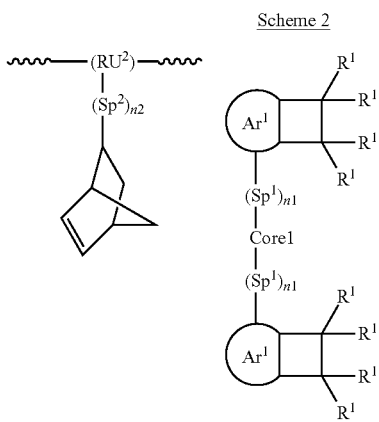

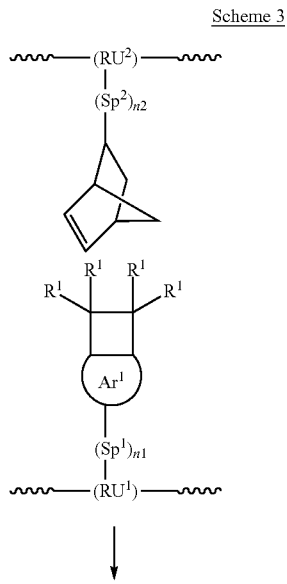

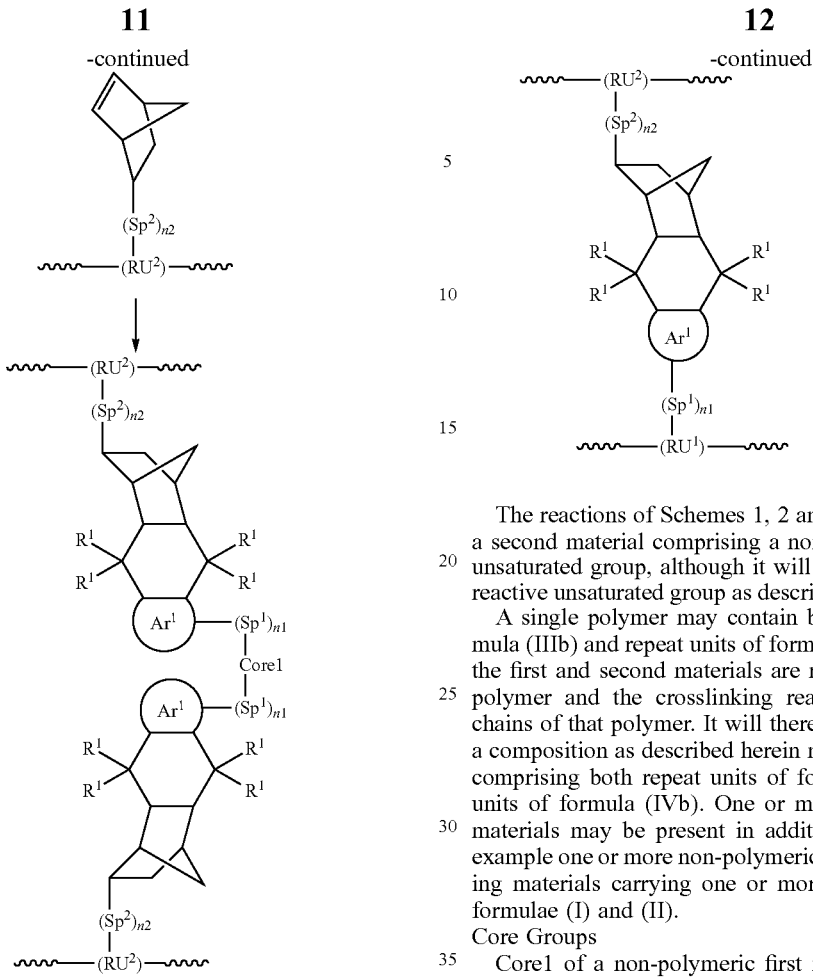

In another embodiment, a non-polymeric compound of formula (IVa) wherein p1 is 2 or more and/or m1 is 2 or more is reacted with a polymer comprising repeat units of formula (IIIb).

Scheme 3 illustrates a crosslinking reaction between a polymer comprising repeat units of formula (IVb) and a polymer comprising repeat units of formula (IIIb):

Scheme 3

The reactions of Schemes 1, 2 and 3 are illustrated using a second material comprising a norbornene as the reactive unsaturated group, although it will be appreciated that any reactive unsaturated group as described herein may be used.

A single polymer may contain both repeat units of formula (IIIb) and repeat units of formula (IVb), in which case the first and second materials are repeat units of the same polymer and the crosslinking reaction may be between chains of that polymer. It will therefore be appreciated that a composition as described herein may be a single polymer comprising both repeat units of formula (IIIb) and repeat units of formula (IVb). One or more further crosslinking materials may be present in addition to the polymer, for example one or more non-polymeric or polymeric crosslinking materials carrying one or more groups selected from formulae (I) and (II).

Core Groups

Core1 of a non-polymeric first material may be substituted only with one or more groups of formula (I) or may be substituted with one or more further substituents.

Core2 of a non-polymeric second material may be substituted only with one or more groups selected from formulae (II) or may be substituted with one or more further substituents.

Exemplary further substituents include $C_{1-40}$ hydrocarbyl groups, for example $C_{1-20}$ alkyl, unsubstituted phenyl and phenyl substituted with one or more $C_{1-20}$ alkyl groups.

Core1 and Core2 may be selected according to the function of the layer that they are to be present in. Optionally, Core1 and Core2 are each independently selected from hole-transporting groups, electron-transporting groups and light-emitting groups.

Exemplary Core1 and Core2 groups include arylene groups, for example benzene and fluorene, and amine groups.

A first non-polymeric compound or second non-polymeric compound may have formula (V):

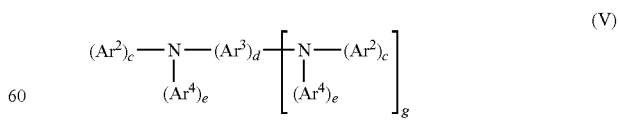

wherein $Ar^2$, $Ar^3$ and $Ar^4$ in each occurrence are independently selected from substituted or unsubstituted aryl or heteroaryl or a group of formula (I) wherein n1=0; g is 0, 1 or 2, preferably 0 or 1; and c, d and e are each independently 1, 2 or 3, wherein at least one of $Ar^2$, $Ar^3$ and $Ar^4$ is substituted with at least one group of formula (I) or (II) and/or at least one of Ar² and Ar⁴ is a group of formula (I) wherein n1=0.

Any two aromatic or heteroaromatic groups selected from Ar², Ar³, Ar⁵, and, if present, Ar⁴ directly bound to the same N atom may be linked by a direct bond or a divalent linking atom or group. Preferred divalent linking atoms and groups include O, S; substituted N; and substituted C.

Preferably, each of Ar², Ar³ and Ar⁴ is independently an aryl group that, in addition to groups of formula (I) and/or (II), may be unsubstituted or substituted with one or more substituents, optionally one or more $C_{1-20}$ alkyl or $C_{1-20}$ alkoxy groups.

Preferably, Ar² and Ar⁴ are each independently phenyl or a group of formula (I) wherein n1=0.

In the case where g=1, Ar³ is preferably $C_{6-20}$ aryl, more preferably phenyl or a polycyclic aromatic group, for example naphthalene, perylene, anthracene or fluorene. If Ar³ is a polycyclic aromatic group then d is preferably 1.

Exemplary non-polymeric first and second compounds include the compounds illustrated below wherein R³ is independently in each occurrence is a substituent, optionally $C_{1-20}$ alkyl, and q is 0, 1, 2, 3 or 4.

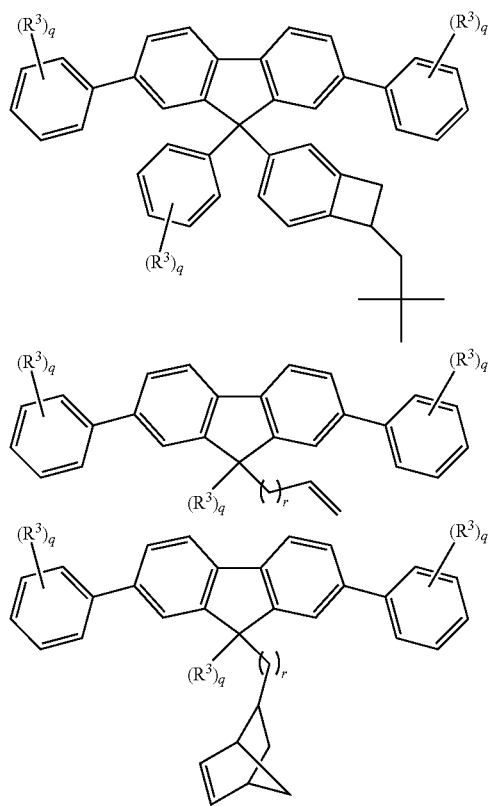

wherein r=1 to 10
Repeat Units

Polymers comprising repeat units RU1 and/or RU2 are preferably copolymers comprising RU1 and/or RU2 and one or more co-repeat units. Co-repeat units preferably do not comprise crosslinkable groups.

Preferably, RU1 and RU2 comprise at least one aromatic or heteroaromatic group, more preferably at least one aromatic group. Preferably, polymers comprising repeat units RU1 and/or RU2 are conjugated polymers.

Optionally, RU1 and RU2 are selected from hole-transporting repeat units, electron-transporting repeat units and light-emitting repeat units.

RU1 and RU2 may be selected according to the function of the layer that they are to be present in or may be used in combination with co-repeat units providing the required functionality. For example, a hole-transporting polymer for use in a hole-transporting layer may contain a hole-transporting repeat unit RU1 or RU2 or may contain a hole-transporting co-repeat unit.

Exemplary repeat units of conjugated polymers are arylene repeat units, arylenevinylene repeat units and arylamine repeat units, each of which may be a co-repeat unit or a repeat unit of formula (IIIb) or (IVb) wherein RU1 or RU2 is arylene, arylenevinylene or arylamine.

One preferred class of arylene repeat units is phenylene repeat units, such as phenylene repeat units of formula (VI):

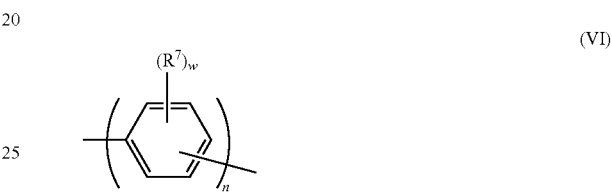

(VI)

wherein w in each occurrence is independently 0, 1, 2, 3 or 4, optionally 1 or 2; n is 1, 2 or 3; and R⁷ independently in each occurrence is a substituent.

Where present, each R⁷ may independently be selected from the group consisting of:
  alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;
  aryl and heteroaryl groups that may be unsubstituted or substituted with one or more substituents, preferably phenyl substituted with one or more $C_{1-20}$ alkyl groups;
  a linear or branched chain of aryl or heteroaryl groups, each of which groups may independently be substituted, for example a group of formula —(Ar⁷)ᵣ wherein each Ar⁷ is independently an aryl or heteroaryl group and r is at least 2, preferably a branched or linear chain of phenyl groups each of which may be unsubstituted or substituted with one or more $C_{1-20}$ alkyl groups; and
  a group of formula (I) or (II).

In the case where R⁷ comprises an aryl or heteroaryl group, or a linear or branched chain of aryl or heteroaryl groups, the or each aryl or heteroaryl group may be substituted with one or more substituents R⁸ selected from the group consisting of:
  alkyl, for example $C_{1-20}$ alkyl, wherein one or more non-adjacent C atoms may be replaced with O, S, substituted N, C=O and —COO— and one or more H atoms of the alkyl group may be replaced with F;
  NR⁹₂, OR⁹, SR⁹, SiR⁹₃ and
  fluorine, nitro and cyano;
wherein each R⁹ is independently selected from the group consisting of alkyl, preferably $C_{1-20}$ alkyl; and aryl or heteroaryl, preferably phenyl, optionally substituted with one or more $C_{1-20}$ alkyl groups.

Substituted N, where present, may be —NR⁶— wherein R⁶ is a substituent and is optionally a $C_{1-40}$ hydrocarbyl group, optionally a $C_{1-20}$ alkyl group.

Preferably, each $R^7$, where present, is independently selected from a group of formula (I) or (II), and $C_{1-40}$ hydrocarbyl. Preferred $C_{1-40}$ hydrocarbyl groups are $C_{1-20}$ alkyl; unsubstituted phenyl; phenyl substituted with one or more $C_{1-20}$ alkyl groups; and a linear or branched chain of phenyl groups, wherein each phenyl may be unsubstituted or substituted with one or more substituents.

If n is 1 then exemplary repeat units of formula (VI) include the following:

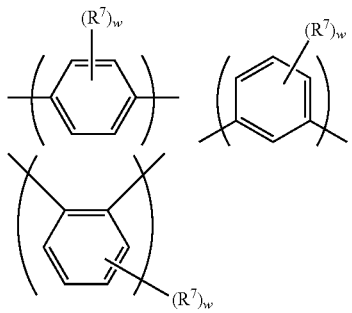

A particularly preferred repeat unit of formula (VI) has formula (VIa):

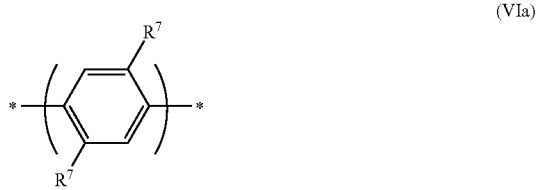

(VIa)

Substituents $R^7$ of formula (VIa) are adjacent to linking positions of the repeat unit, which may cause steric hindrance between the repeat unit of formula (VIa) and adjacent repeat units, resulting in the repeat unit of formula (VIa) twisting out of plane relative to one or both adjacent repeat units.

Exemplary repeat units where n is 2 or 3 include the following:

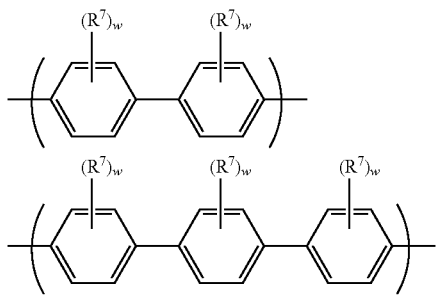

A preferred repeat unit has formula (VIb):

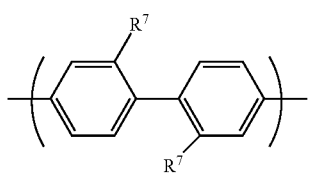

(VIb)

The two $R^7$ groups of formula (VIb) may cause steric hindrance between the phenyl rings they are bound to, resulting in twisting of the two phenyl rings relative to one another.

A further class of arylene repeat units is optionally substituted fluorene repeat units, such as repeat units of formula (VII):

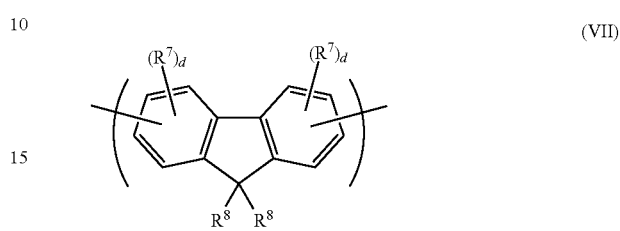

(VII)

wherein $R^8$ in each occurrence is the same or different and is a substituent wherein the two groups $R^8$ may be linked to form a ring; $R^7$ is a substituent as described above; and d is 0, 1, 2 or 3.

Each $R^8$ may independently be selected from the group consisting of:
alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;
aryl and heteroaryl groups that may be unsubstituted or substituted with one or more substituents, preferably phenyl substituted with one or more $C_{1-20}$ alkyl groups;
a linear or branched chain of aryl or heteroaryl groups, each of which groups may independently be substituted, for example a group of formula —$(Ar^7)_r$ wherein each $Ar^7$ is independently an aryl or heteroaryl group and r is at least 2, optionally 2 or 3, preferably a branched or linear chain of phenyl groups each of which may be unsubstituted or substituted with one or more $C_{1-20}$ alkyl groups; and
a group of formula (I) or (II).

Preferably, each $R^8$ is independently a group of formula (I) or (II) or a $C_{1-40}$ hydrocarbyl group. Preferred $C_{1-40}$ hydrocarbyl groups are $C_{1-20}$ alkyl; unsubstituted phenyl; phenyl substituted with one or more $C_{1-20}$ alkyl groups; and a linear or branched chain of phenyl groups, wherein each phenyl may be unsubstituted or substituted with one or more substituents.

Substituted N, where present, may be —$NR^6$— wherein $R^6$ is as described above.

The aromatic carbon atoms of the fluorene repeat unit may be unsubstituted, or may be substituted with one or more substituents $R^7$ as described with reference to Formula (VI).

Exemplary substituents $R^7$ are alkyl, for example $C_{1-20}$ alkyl, wherein one or more non-adjacent C atoms may be replaced with O, S, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

The extent of conjugation of repeat units of formula (VII) to aryl or heteroaryl groups of adjacent repeat units in the polymer backbone may be controlled by (a) linking the repeat unit through the 3- and/or 6-positions to limit the extent of conjugation across the repeat unit, and/or (b)

substituting the repeat unit with one or more substituents $R^7$ in or more positions adjacent to the linking positions in order to create a twist with the adjacent repeat unit or units, for example a 2,7-linked fluorene carrying a $C_{1-20}$ alkyl substituent in one or both of the 3- and 6-positions.

The repeat unit of formula (VII) may be a 2,7-linked repeat unit of formula (VIIa):

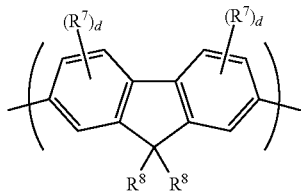

(VIIa)

A relatively high degree of conjugation across the repeat unit of formula (VIIa) may be provided in the case where each d=0, or where any substituent $R^7$ is not present at a position adjacent to the linking 2- or 7-positions of formula (VIIa).

A relatively low degree of conjugation across the repeat unit of formula (VIIa) may be provided in the case where at least one d is at least 1, and where at least one substituent $R^7$ is present at a position adjacent to the linking 2- or 7-positions of formula (VIIa). Optionally, each d is 1 and the 3- and/or 6-position of the repeat unit of formula (VIIa) is substituted with a substituent $R^7$ to provide a relatively low degree of conjugation across the repeat unit.

The repeat unit of formula (VII) may be a 3,6-linked repeat unit of formula (VIIb)

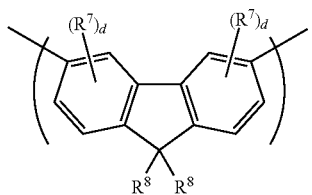

(VIIb)

The extent of conjugation across a repeat unit of formula (VIIb) may be relatively low as compared to a corresponding repeat unit of formula (VIIa).

Another exemplary arylene repeat unit has formula (VIII):

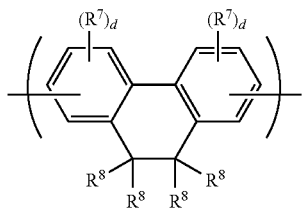

(VIII)

wherein $R^7$, $R^8$ and d are as described with reference to formulae (VI) and (VII) above. Any of the $R^7$ groups may be linked to any other of the $R^7$ groups to form a ring. The ring so formed may be unsubstituted or may be substituted with one or more substituents, optionally one or more $C_{1-20}$ alkyl groups.

Repeat units of formula (VIII) may have formula (VIIIa) or (VIIIb):

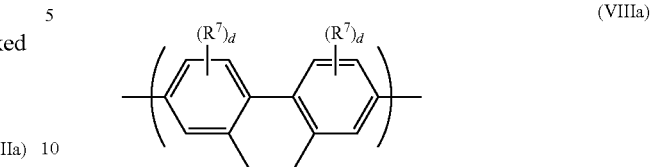

(VIIIa)

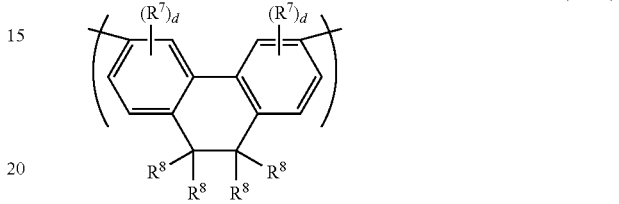

(VIIIb)

The one or more co-repeat units may include a conjugation-breaking repeat unit, which is a repeat unit that does not provide any conjugation path between repeat units adjacent to the conjugation-breaking repeat unit.

Exemplary conjugation-breaking co-repeat units include co-repeat units of formula (IX):

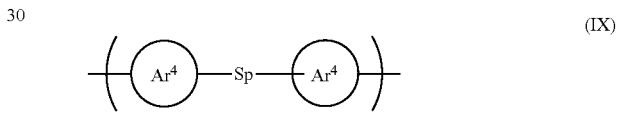

(IX)

wherein:

$Ar^4$ in each occurrence independently represents an aryl or heteroaryl group that may be unsubstituted or substituted with one or more substituents; and Sp represents a spacer group comprising at least one carbon or silicon atom.

Preferably, the spacer group Sp includes at least one $sp^3$-hybridised carbon atom separating the $Ar^4$ groups.

Preferably $Ar^4$ is an aryl group and the $Ar^4$ groups may be the same or different. More preferably each $Ar^4$ is phenyl.

Each $Ar^4$ may independently be unsubstituted or may be substituted with 1, 2, 3 or 4 substituents. The one or more substituents may be selected from:

$C_{1-20}$ alkyl wherein one or more non-adjacent C atoms of the alkyl group may be replaced by O, S or COO, C=O, $NR^6$ or $SiR^6_2$ and one or more H atoms of the $C_{1-20}$ alkyl group may be replaced by F wherein $R^6$ is a substituent and is optionally in each occurrence a $C_{1-40}$ hydrocarbyl group, optionally a $C_{1-20}$ alkyl group; and aryl or heteroaryl, optionally phenyl, that may be unsubstituted or substituted with one or more $C_{1-20}$ alkyl groups.

Preferred substituents of $Ar^4$ are $C_{1-20}$ alkyl groups, which may be the same or different in each occurrence.

Exemplary groups Sp include a $C_{1-20}$ alkyl chain wherein one or more non-adjacent C atoms of the chain may be replaced with O, S, —$NR^6$—, —$SiR^6_2$—, —C(=O)— or —COO— and wherein $R^6$ in each occurrence is a substituent and is optionally in each occurrence a $C_{1-40}$ hydrocarbyl group, optionally a $C_{1-20}$ alkyl group. Preferably, Sp contains at least one sp3-hybridised carbon atom spacing the two groups $Ar^4$ apart.

A polymer comprising a repeat unit RU1 and/or RU2 may comprise arylamine repeat units of formula (X), either as a co-repeat unit or a repeat unit of formula (IIIb) or (IVb):

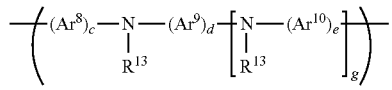
(X)

wherein $Ar^8$, $Ar^9$ and $Ar^{10}$ in each occurrence are independently selected from substituted or unsubstituted aryl or heteroaryl, g is 0, 1 or 2, preferably 0 or 1, $R^{13}$ independently in each occurrence is H or a substituent, preferably a substituent, and c, d and e are each independently 1, 2 or 3.

Repeat units of formula (X) may provide the polymer with hole-transporting properties for use in a hole-transporting layer or light-emitting layer, and/or light-emitting properties for use in a light-emitting layer $R^{13}$, which may be the same or different in each occurrence when g is 1 or 2, is preferably selected from the group consisting of alkyl, for example $C_{1-20}$ alkyl, $Ar^{11}$, a branched or linear chain of $Ar^{11}$ groups, or a group of formula (I) or (II), wherein $Ar^{11}$ in each occurrence is independently optionally substituted aryl or heteroaryl.

Any two aromatic or heteroaromatic groups selected from $Ar^8$, $Ar^9$, and, if present, $Ar^{10}$ and $Ar^{11}$ directly bound to the same N atom may be linked by a direct bond or a divalent linking atom or group to another of $Ar^8$, $Ar^9$, $Ar^{10}$ and $Ar^{11}$. Preferred divalent linking atoms and groups include O, S; substituted N; and substituted C.

$Ar^8$ and $Ar^{10}$ aryl, more preferably phenyl, that may be are preferably $C_{6-20}$ unsubstituted or substituted with one or more substituents.

In the case where g=0, $Ar^9$ is preferably $C_{6-20}$ aryl, more preferably phenyl, that may be unsubstituted or substituted with one or more substituents.

In the case where g=1, $Ar^9$ is preferably $C_{6-20}$ aryl, more preferably phenyl or a polycyclic aromatic group, for example naphthalene, perylene, anthracene or fluorene, that may be unsubstituted or substituted with one or more substituents.

$R^{13}$ is preferably $Ar^{11}$ or a branched or linear chain of $Ar^{11}$ groups. $Ar^{11}$ in each occurrence is preferably phenyl that may be unsubstituted or substituted with one or more substituents.

Exemplary groups $R^{13}$ include the following, each of which may be unsubstituted or substituted with one or more substituents, and wherein * represents a point of attachment to N:

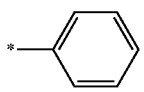 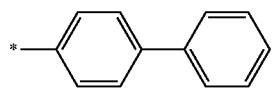

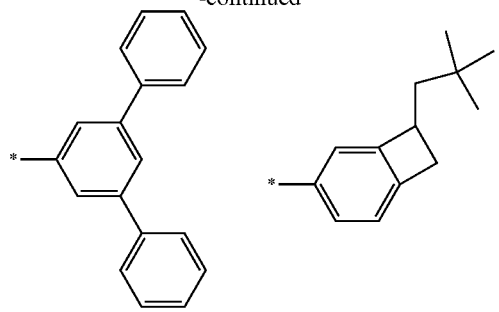

c, d and e are preferably each 1.

$Ar^8$, $Ar^9$, and, if present, $Ar^{10}$ and $Ar^{11}$ are each independently unsubstituted or substituted with one or more, optionally 1, 2, 3 or 4, substituents. Exemplary substituents may be selected from:

substituted or unsubstituted alkyl, optionally $C_{1-20}$ alkyl, wherein one or more non-adjacent C atoms may be replaced with optionally substituted aryl or heteroaryl (preferably phenyl), O, S, C=O or —COO— and one or more H atoms may be replaced with F; and a group of formula (I) or (II).

Preferred substituents of $Ar^8$, $Ar^9$, and, if present, $Ar^{10}$ and $Ar^{11}$ are $C_{1-40}$ hydrocarbyl, preferably $C_{1-20}$ alkyl or a group of formula (I) or (II).

Preferred repeat units of formula (X) include unsubstituted or substituted units of formulae 1-3:

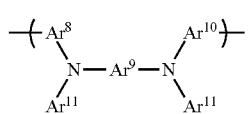
1

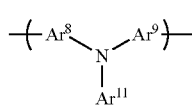
2

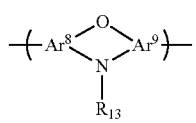
3

Preferably, $Ar^8$, $Ar^{10}$ and $Ar^{11}$ of repeat units of formula 1 are phenyl and $Ar^9$ is phenyl or a polycyclic aromatic group.

Preferably, $Ar^8$, $Ar^9$ and $Ar^{11}$ of repeat units of formulae 2 and 3 are phenyl.

Preferably, $Ar^8$ and $Ar^9$ of repeat units of formula 3 are phenyl and $R^{13}$ is phenyl or a branched or linear chain of phenyl groups.

A hole-transporting polymer comprising repeat units of formula (X) may be a homopolymer or a copolymer containing repeat units of formula (X) and one or more co-repeat units.

Repeat units of formula (X) may be provided in a molar amount in the range of about 10 mol % up to about 95 mol %, optionally about 10-75 mol % or about 10-50 mol %.

The polymer may contain one or two or more different repeat units of formula (X).

Exemplary polymeric repeat units of formulae (IIIb) and (IVb) are illustrated below.

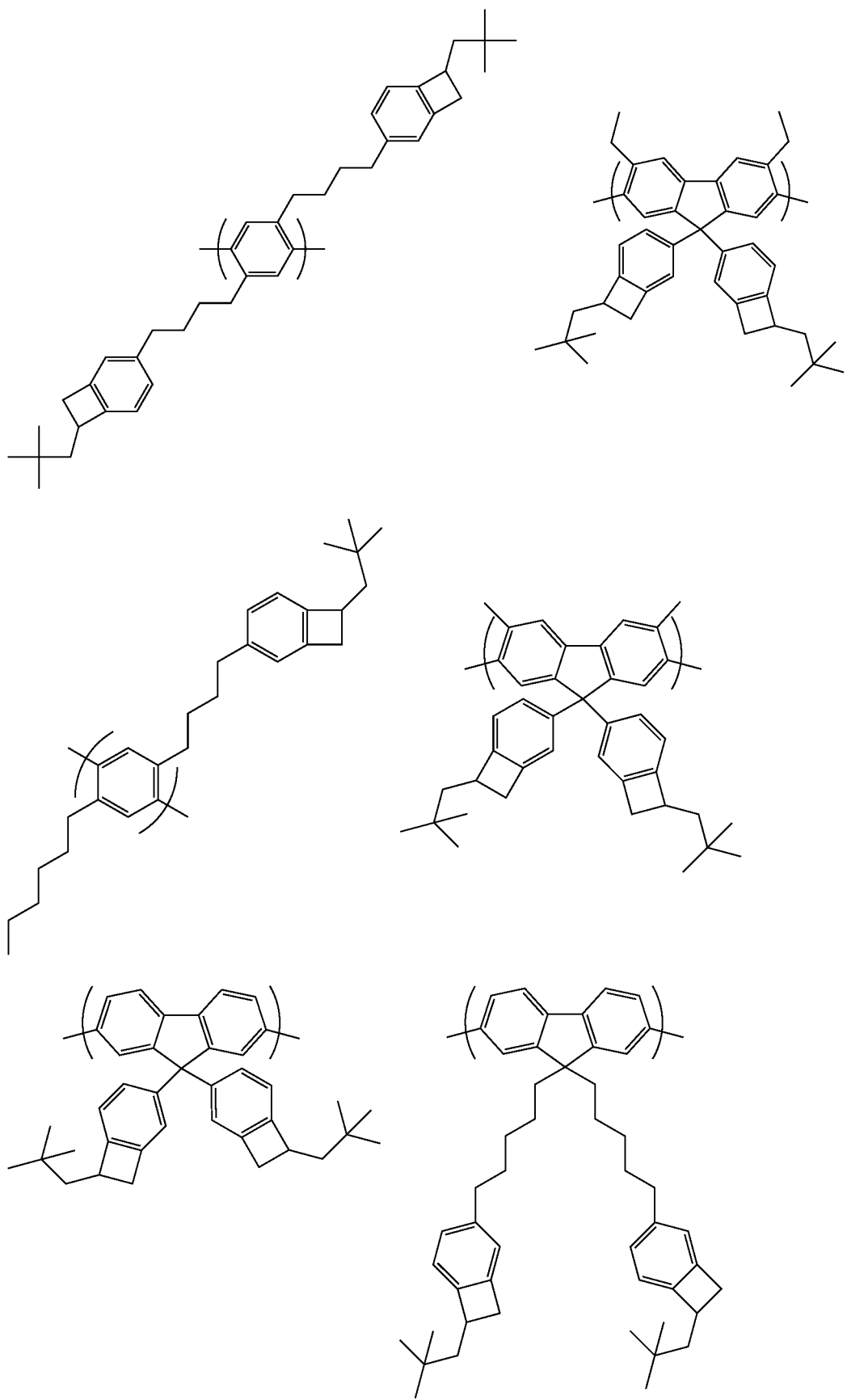

-continued
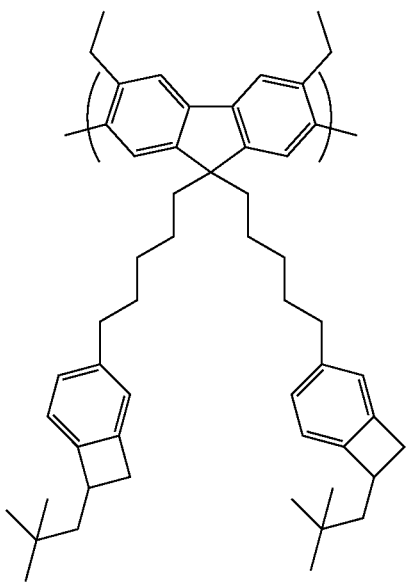
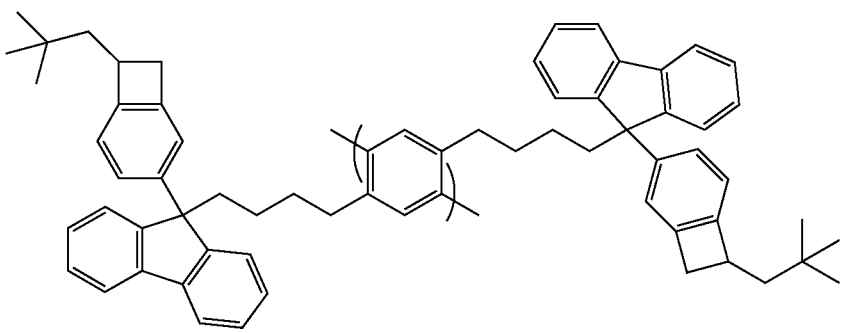
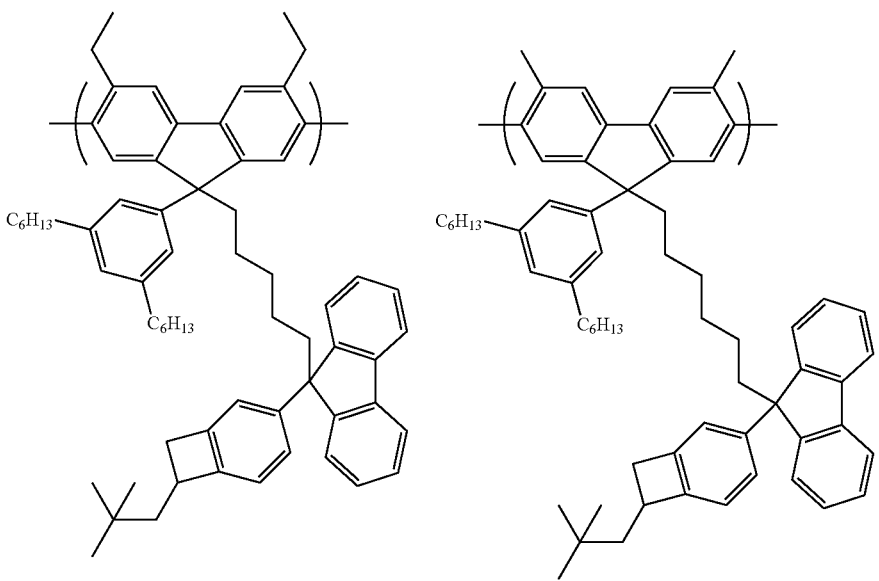

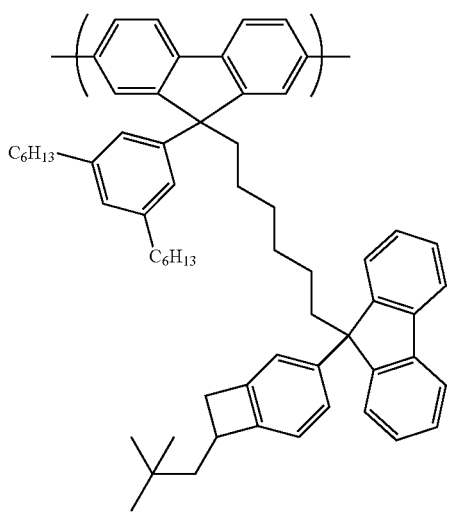
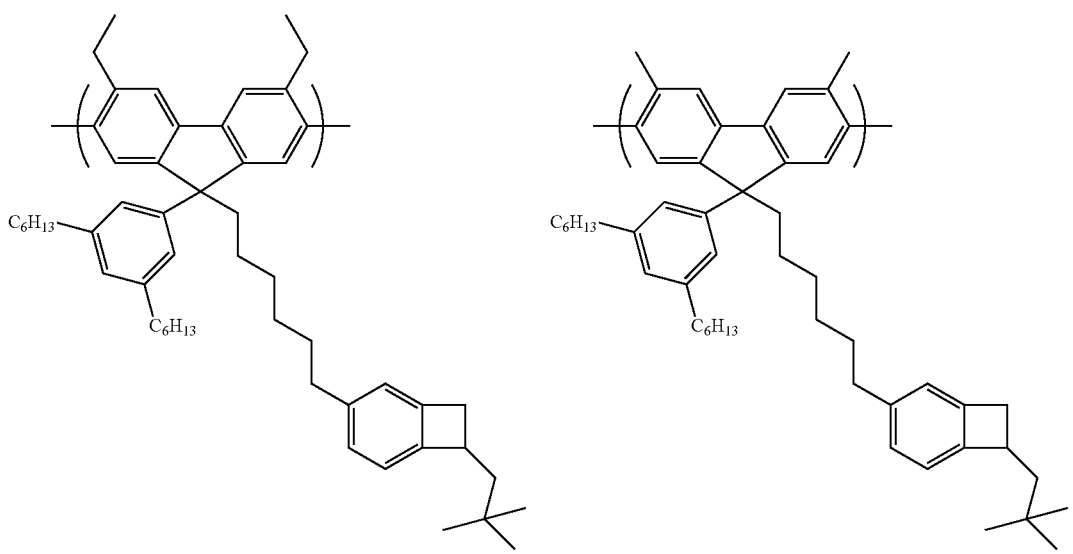
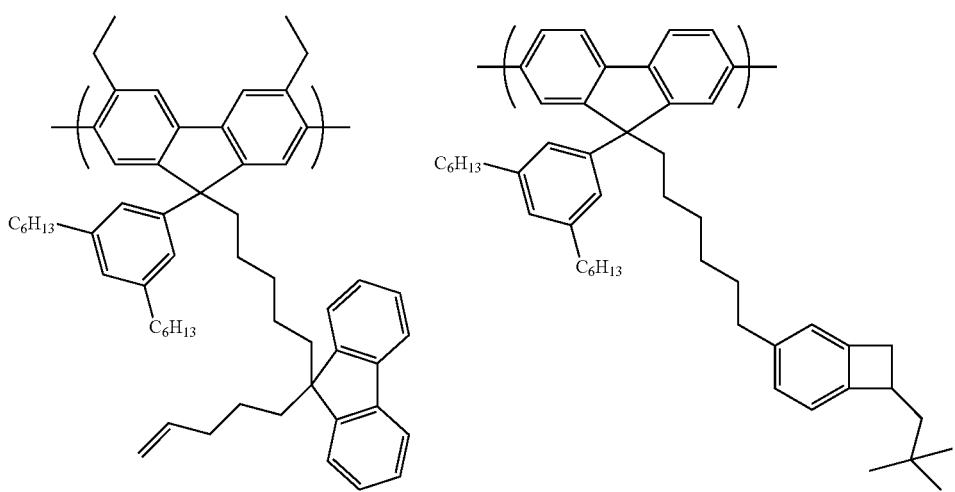

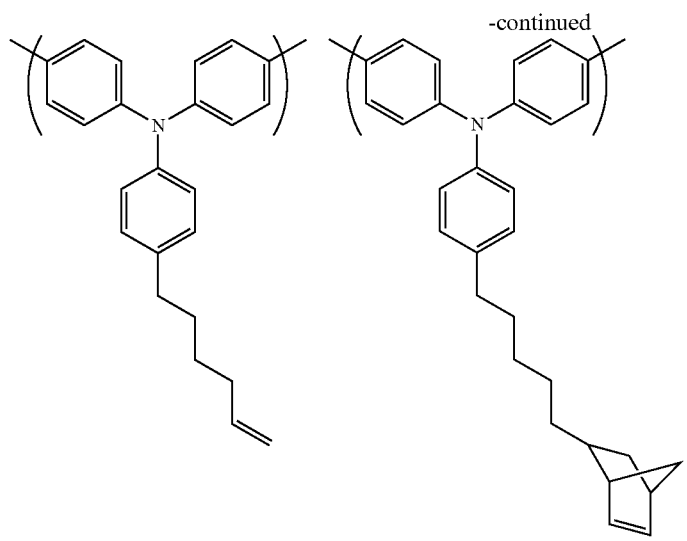
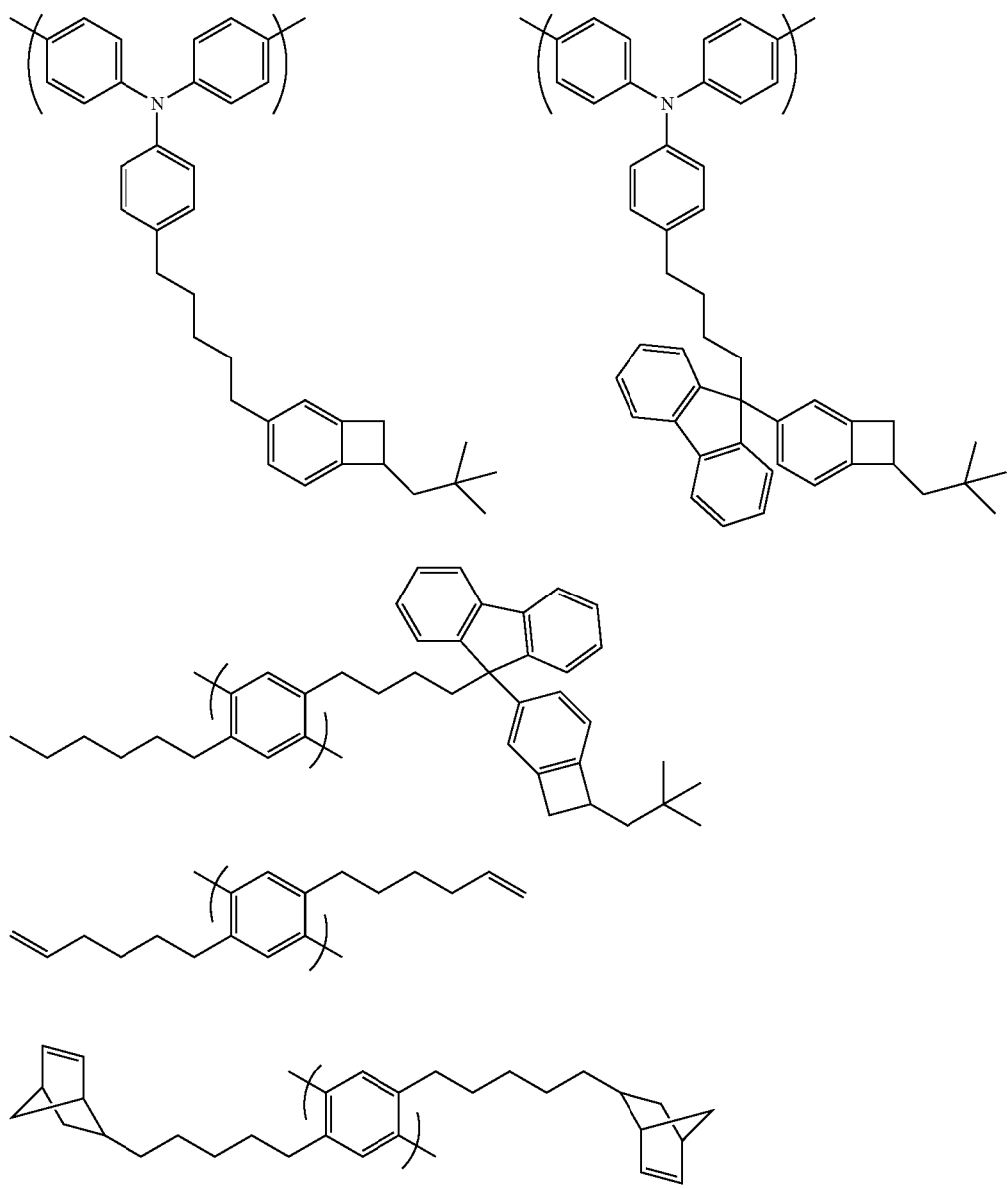

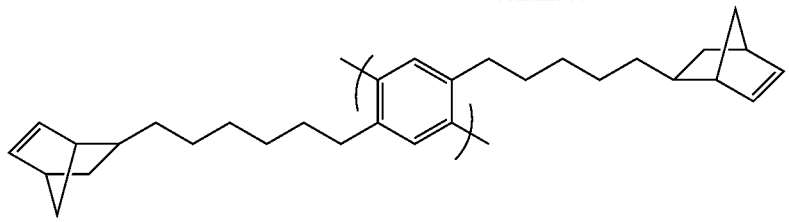
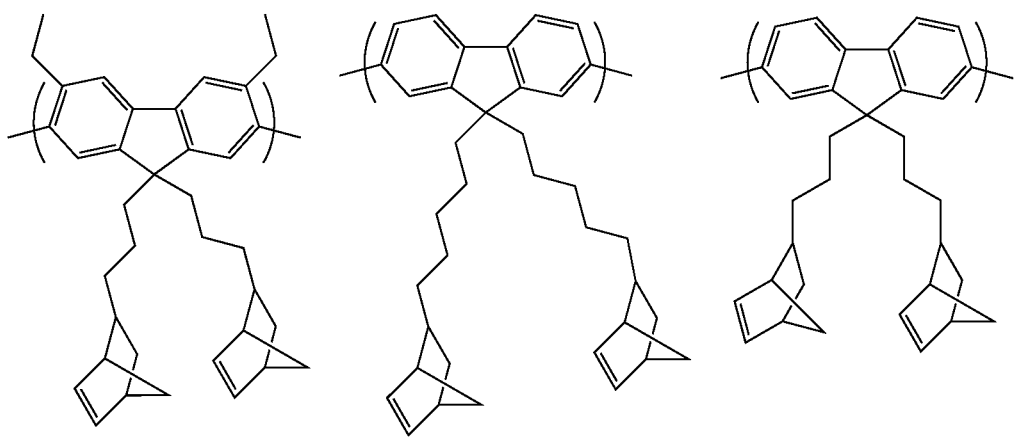
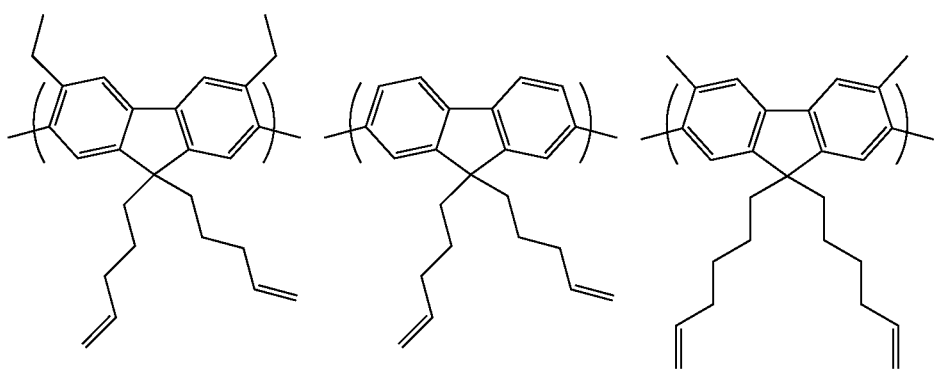
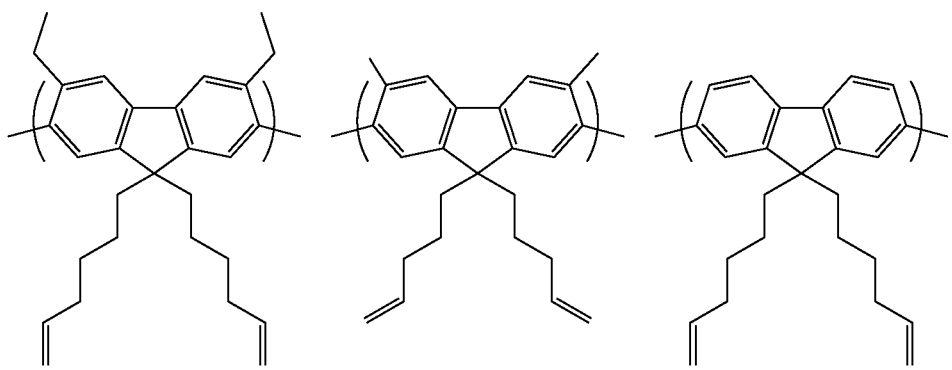

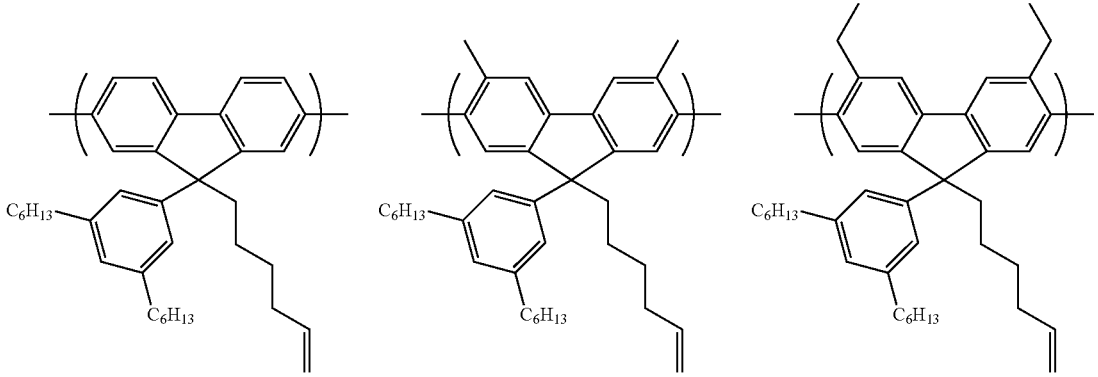

Polymers as described herein suitably have a polystyrene-equivalent number-average molecular weight (Mn) measured by gel permeation chromatography in the range of about $1\times10^3$ to $1\times10^8$, and preferably $1\times10^3$ to $5\times10^6$. The polystyrene-equivalent weight-average molecular weight (Mw) of the polymers described herein may be $1\times10^3$ to $1\times10^8$, and preferably $1\times10^4$ to $1\times10^7$.

The polymers as described anywhere herein are suitably amorphous polymers.

Polymer Synthesis

Preferred methods for preparation of conjugated polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable π—Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halogen, other leaving groups capable of participating in metal insertion include groups include tosylate, mesylate and triflate.

Hole Injection Layers

A conductive hole injection layer, which may be formed from a conductive organic or inorganic material, may be provided between the anode 103 and the hole-transporting layer 105 of an OLED as illustrated in FIG. 1 to assist hole injection from the anode into the layer or layers of semiconducting polymer. Examples of doped organic hole injection materials include optionally substituted, doped poly (ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Cathode

The cathode 109 is selected from materials that have a workfunction allowing injection of electrons into the light-emitting layer of the OLED. Other factors influence the selection of the cathode such as the possibility of adverse interactions between the cathode and the light-emitting material. The cathode may consist of a single material such as a layer of aluminium. Alternatively, it may comprise a plurality of conductive materials such as metals, for example a bilayer of a low work function material and a high work function material such as calcium and aluminium, for example as disclosed in WO 98/10621. The cathode may comprise elemental barium, for example as disclosed in WO 98/57381, Appl. Phys. Lett. 2002, 81(4), 634 and WO 02/84759. The cathode may comprise a thin (e.g. 1-5 nm) layer of metal compound, in particular an oxide or fluoride of an alkali or alkali earth metal, between the organic layers of the device and one or more conductive cathode layers to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a work function of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming a layer of an organic electronic device, preferably a layer of an OLED, more preferably a hole-transporting layer of an OLED, may comprise a material having a substituent of formula (I) and one or more suitable solvents. The formulation may consist essentially of the first material and the one or more solvents, or may contain one or more further components, for example one or more materials having a substituent of formula (II).

In the case of an OLED hole-transporting layer, a light-emitting layer may be formed on the hole-transporting layer by a solution deposition technique as described herein.

The formulation may be a solution of the material having a substituent of formula (I) in the one or more solvents, or may be a dispersion in the one or more solvents in which one or more components are not dissolved. Preferably, the formulation is a solution.

Solvents suitable for dissolving a material having a substituent of formula (I), particularly compositions containing polymers comprising alkyl substituents, include benzenes substituted with one or more substituents selected from $C_{1-10}$ alkyl, $C_{1-10}$ alkoxy and chlorine, for example toluene, xylenes and methylanisoles.

Particularly preferred solution deposition techniques include printing and coating techniques such as spin-coating and inkjet printing. Inkjet printing is preferred.

Spin-coating is particularly suitable for devices wherein patterning of the light-emitting layer is unnecessary—for example for lighting applications or simple monochrome segmented displays.

Inkjet printing is particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). The patterned layer is preferably a layer of photoresist that is patterned to define wells as described in, for example, EP 0880303. A hole-transporting layer may be formed by inkjet printing a material having a substituent of formula (I) into the wells of the patterned layer and reacting, preferably crosslinking, the material. The light-emitting material or materials may then be inkjet printed into the wells on the hole-transporting layer.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, flexographic printing and screen printing.

Applications

The first material and compositions thereof as described herein may be used to form one or more layers of organic electronic devices. Preferably, the first material is used to form a crosslinked layer onto which a further layer is formed by a solution deposition method.

First materials and layer formation methods as described herein may be used to form a charge-transporting layer or light-emitting layer of an OLED; a semiconducting layer of an organic photoresponsive device, for example a photosensor or a photovoltaic device; and a semiconducting layer or dielectric layer of an organic thin film transistor.

An organic photoresponsive device may comprise an anode, a cathode and a semiconducting layer formed from a composition as described herein between the anode and the cathode. The organic semiconducting layer may be an electron accepting layer, an electron-donating layer, or a further layer between the anode and the cathode. A single layer containing a blend of an electron-accepting material and an electron-donating material may be provided in place of separate accepting and donating layers, and this layer may be crosslinked by substituting one or more components of this layer with at least one substituent of formula (I) and optionally at least one substituent of formula (II).

An organic thin film transistor may comprise source and drain electrodes; an organic semiconductor layer extending between and in electrical contact with the source and drain electrodes; a gate electrode; and a dielectric layer between the organic semiconducting layer and the gate electrode.

EXAMPLES

Compound Example 1

Non-polymeric Compound Example 1 was prepared according to the following reaction scheme:

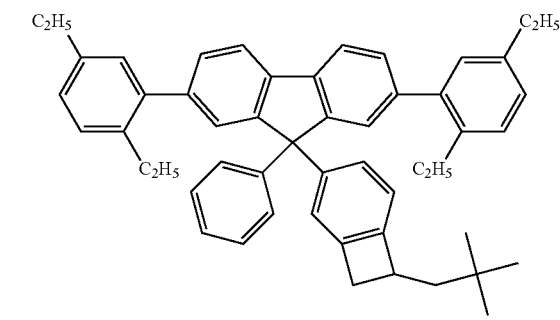 [SMILES: CCc1ccc(CC)c(-c2ccc3c(c2)C(c2ccccc2)(c2ccc4c(c2)CC4CC(C)(C)C)c2cc(-c4cc(CC)ccc4CC)ccc2-3)c1]

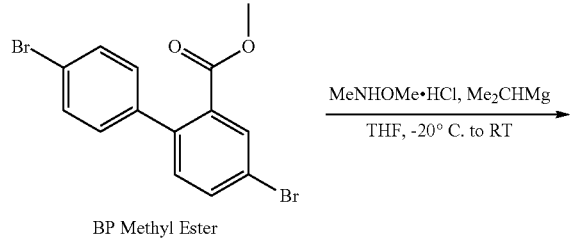

BP Methyl Ester

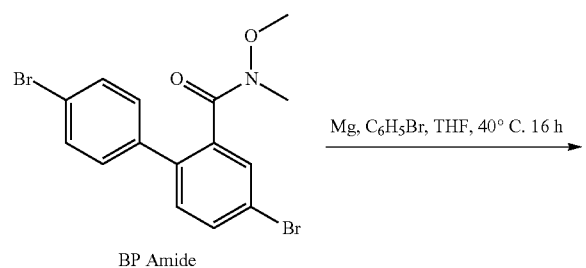

BP Amide

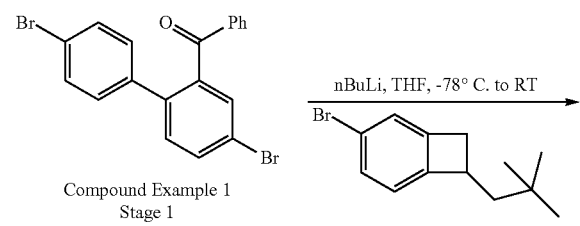

Compound Example 1
Stage 1

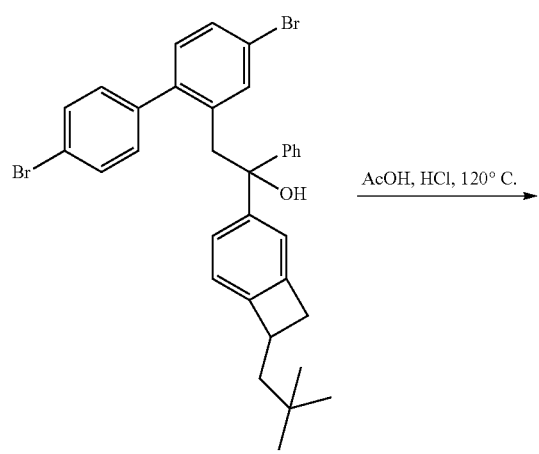

Compound Example 1
Stage 2

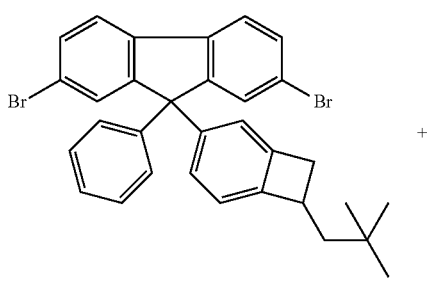

Compound Example 1
Stage 3

+

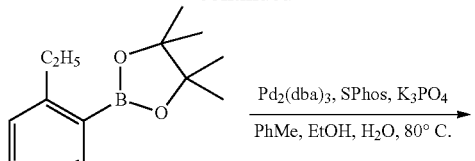

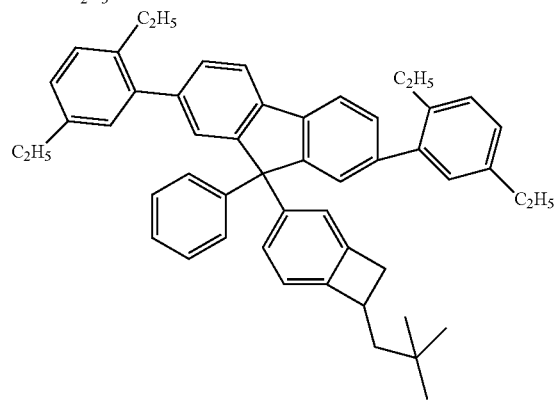

Compound Example 1

BP Amide

To a solution of BP methyl ester (250 g, 0.68 mol) and N,O-dimethyl hydroxylamine.HCl (102.1 g, 1.05 mol) in THF (1250 ml) at −20° C. under nitrogen was added drop wise a solution of isopropylmagnesium chloride (2M in THF) (1047 ml, 2.09 mol) so as to keep the internal temperature <−5° C., the reaction mixture was allowed to warm to room temperature and stirred for a further 16 hr. The reaction mixture was cooled to 0° C., quenched with dilute hydrochloric acid (1.5 M), diluted with ethyl acetate (3 L), the ethyl acetate layer was separated, dried ($Na_2SO_4$) and the solvent removed under reduced pressure. The resulting white solid was triturated with methanol, filtered and washed with hot methanol and hot ACN to give the BP Amide (196 g, 73% yield, HPLC purity of 98.4%

$^1$H-NMR (400 MHz, $CDCl_3$): δ [ppm] 3.12 (s, 3H), 3.33 (s, 3H), 7.25-7.35 (m, 3H), 7.52-7.54 (m, 2H), 7.60-7.62 (m, 2H).

$^{13}$C-NMR (100 MHz, $CDCl_3$): δ [ppm] 32.45, 61.29, 121.30, 122.19, 129.81, 129.93, 130.82, 131.63, 132.54, 136.43, 137.31, 138.34, 169.79.

Compound 1 Example 1 Stage 1

To a suspension of magnesium turnings (25 g, 1.04 mol), iodine and 1,2-dibromoethane in dry diethyl ether (650 ml) at room temperature under nitrogen, was added bromo benzene (14.5 ml. 0.14 mol), once initiated the remaining bromo benzene (29 ml, 0.28 mol) was added drop wise, the reaction mixture stirred at 40° C. for 16 hr and then allowed to cool to room temperature. The resulting Grignard reagent was added drop wise to a solution of the BP amide (75 g, 0.19 mol) in dry THF (750 ml) at −20° C. and stirring continued at this temperature for a further 30 mins. It was then cooled to 0° C., quenched with dilute hydrochloric acid (1 L, 1.5 M), warmed to room temperature, diluted with ethyl acetate, the organic layer was separated, dried ($Na_2SO_4$) and the solvent removed under reduced pressure. The resulting white solid was triturated with methanol twice, filtered and washed with hot methanol to give Compound Example 1 Stage 1 (68 g, 87% yield, HPLC purity 97.7%).

$^1$H-NMR (400 MHz, CDCl$_3$): δ$_H$ [ppm] 7.07-7.10 (m, 2H), 7.25-7.35 (m, 5H), 7.45-7.49 (m, 1H), 7.61-7.68 (m, 3H), 7.69-7.70 (m, 1H).

Compound Example 1 Stage 2

To a solution of Monomer Example 1 Stage 2 (18.2 g, 0.072 mol) in dry tetrahydrofuran (150 ml) at −78° C. under nitrogen, was added drop wise a solution of n-butyl lithium (2.5M in hexane, 28.8 ml, 0.072 mol) so as to maintain an internal temperature of <−74° C. The reaction mixture was stirred for 2 hr, then a solution of the BP amide (20 g, 0.048 mol) was added drop wise as so as to keep the internal temperature <−74° C. and the mixture stirred at this temperature for 1 hr. The mixture was allowed to warm up slowly to room temperature over night; it was then cooled to 5° C., quenched by the drop wise addition of a dilute solution of HCl (50 ml, 1.5 M) and extracted with ethyl acetate (500 ml), (dried (Na$_2$SO$_4$) and the solvent removed under reduced pressure. Purification by silica column chromatography (2% EtOAc in hexane) delivered the title compound (18.2 g, 68% yield).

Compound Example 1 Stage 3

A solution of Compound Example 1 Stage 2 (16.3 g, 0.028 mol), glacial AcOH (245 ml) and concentrated HCl (4.9 ml) under nitrogen was heated at 120° C. for 1 hr. The mixture was cooled, poured carefully onto a solution of ice:water (500 ml) and the resulting solid was isolated by filtration and dried. The aqueous phase was extracted with dichloromethane, the combined organic extracts dried (Na$_2$SO$_4$) and the solvent removed under reduced pressure. Purification by silica column chromatography (5% EtOAc in hexane) delivered the title compound (14.3 g, 48% yield, HPLC purity 54%).

Compound Example 1

A solution of Compound Example 1 Stage 3 (14.3 g, 0.025 mol), 2-(2,5-diethylphenyl)-4,4,5,5-tetrsmethyl-1,3,2-dioxaborolane (19.5 g, 0.075 mol), potassium phosphate tribasic (23 g, 0.1 mmol), toluene (170 ml), ethanol (57 ml) and distilled water (57 ml) was purged with argon for 30 mins, Pd$_2$(dba)$_3$ (0.195 g, 0.0002 mol) and SPhos (0.195 g, 0.0004 mol) were added and the reaction mixture heated at 100° C. for 16 hr. The mixture was cooled down to room temperature, filtered through a celite plug (ethyl acetate 500 ml), diluted with water (500 ml), the organic phase separated, washed with brine (500 ml), dried (Na$_2$SO$_4$) and the solvent removed under reduced pressure. Purification by silica column chromatography (hexane) followed by reaction with Pd/C in ethyl acetate and purification using reverse phase chromatography (acetonitrile:THF) gave Compound Example 1 as a white solid (4 g, 24% yield, HPLC purity 99.3%).

$^1$H-NMR (400 MHz, CDCl$_3$): δ$_H$ [ppm] 0.94 (s, 9H), 1.06 (t, J=7.48 Hz, 6H), 1.28 (t, J=7.60 Hz, 6H), 1.51-1.58 (m, 2H), 1.72-1.76 (m, 1H), 2.56 (q, J=7.44 Hz, 4H), 2.68 (q, J=7.64 Hz, 4H), 3.26-3.29 (m, 1H), 3.46-3.49 (m, 1H), 6.89-6.94 (m, 2H), 7.09-7.15 (m, 3H), 7.18-7.26 (m, 8H), 7.28-7.30 (m, 1H), 7.36 (d, J=7.76 Hz, 2H), 7.44 (s, 2H), 7.83 (d, J=7.76 Hz, 2H).

$^{13}$C-NMR (400 MHz, CDCl$_3$): δ$_H$ [ppm] 15.52, 15.79, 25.89, 28.35, 29.79, 29.87, 31.04, 38.03, 39.93, 48.38, 65.94, 119.71, 121.52, 122.62, 126.42, 126.73, 126.89, 127.36, 128.07, 128.21, 128.56, 128.81, 129.51, 138.51, 138.97, 141.29, 141.44, 141.64, 143.64, 144.82, 146.48, 148.56, 151.35

Monomer Example 1

Monomer Example 1 was prepared according to the following reaction scheme:

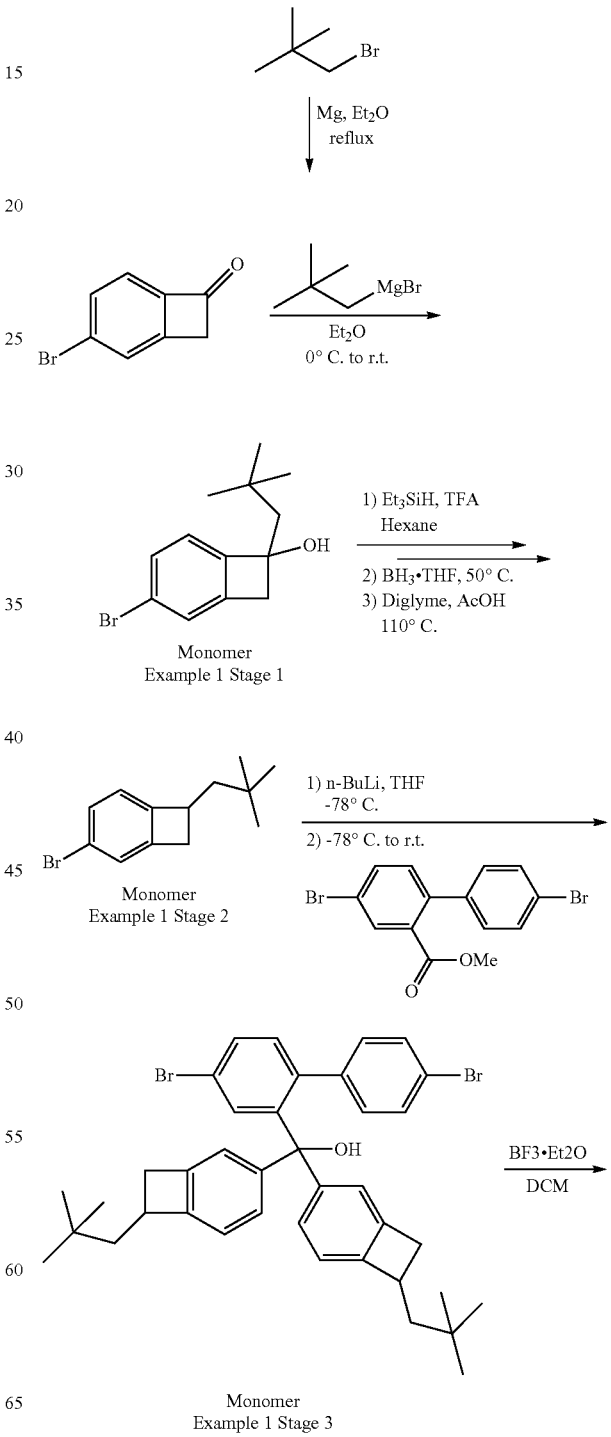

Monomer Example 1 Stage 1

Monomer Example 1 Stage 2

Monomer Example 1 Stage 3

-continued

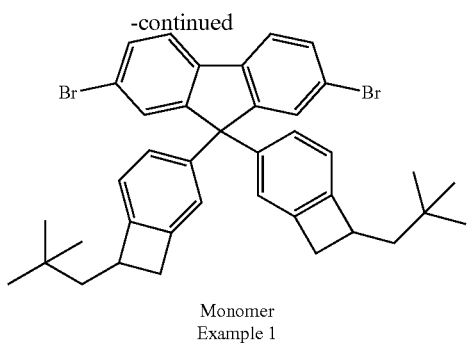

Monomer
Example 1

Monomer Example 1 Stage 1

To a suspension of magnesium turnings (15.42 g, 634 mmol) and iodine (3 pellets) in dry diethyl ether (10 ml) at room temperature under nitrogen, was added a solution of neopentyl bromide (77 ml, 601 mmol) in dry diethyl ether (290 ml) dropwise over 2 hr so as to maintain a gentle reflux, then the mixture was refluxed for 1 hr and then allowed to cool to room temperature. The resulting Grignard reagent was added dropwise to a solution of 3-bromobicyclo[4.2.0] octa-1,3,5-trien-7-one (100 g, 510 mmol) in dry diethyl ether (1000 ml) so as to maintain an internal temperature of ~0° C. The reaction mixture was allowed to warm to room temperature overnight, it was then cooled to 0° C., quenched with dilute hydrochloric acid (340 ml, 2M aq), and allowed to warm to room temperature. The organic phase was separated washed with water (3×120 ml), dried over MgSO$_4$ and the solvent removed under reduced pressure to give an orange oil (134 g). The oil was purified by a silica plug (eluting with hexane:ethyl acetate (95:5%)) to give the title compound as an orange oil as a mixture of two isomers (111.1 g, 0.40 mol, 78% yield, 91.8% pure by $^1$H NMR).

MS (EI) m/z 270 ((Br$^{81}$) M$^+$, 2%), 268 ((Br$^{79}$) M$^+$, 2), 255 ((Br$^{81}$) M$^+$–OH, 11), 253 ((Br$^{79}$) M$^+$–OH, 11), 199 ((Br$^{81}$) M$^+$-neopentyl, 100), 197 ((Br$^{79}$) M$^+$-neopentyl, 99)

$^1$H-NMR (600 MHz, CDCl$_3$): $\delta_H$ [ppm] 1.10 (9H, s), 1.81 (d, J=14.7 Hz, 1H), 1.94 (d, J=14.7 Hz, 1H), 3.16 (d, J=14.4 Hz, 1H), 3.48 (d, J=14.4 Hz, 1H), 7.07 (d, J=7.6 Hz, 1H), 7.29 (s, 1H), 7.37 (d, J=7.6 Hz, 1H), Monomer Example 1 Stage 2

Trifluoroacetic acid (159 ml, 2062 mmol) was added dropwise over a 1 hr period to a solution of Monomer Example 1 Stage 1 (111 g, 395 mmol) and triethylsilane (67 ml, 416 mmol) in hexane (325 ml) at 0° C. under nitrogen. The reaction was warmed to room temperature and stirred for 24 hrs. The reaction mixture was poured into a solution of ice:water (2.3 L) and stirred for 1 hr until the ice had melted and the layers had separated. The aqueous phase was extracted with hexane (500 ml), the combined organic extracts were washed with water (3×600 ml), sodium acetate (10% wt:vol, 500 ml), water (3×600 ml), dried over MgSO$_4$ and the solvent removed under reduced pressure to give an orange oil (152.7 g). The oil was purified by a silica plug (eluting with hexane) to give the title compound as a yellow oil (103.64 g, 376 mmol, 91.8% pure by $^1$H NMR (as a mixture of two isomers and containing 2% of an alkene impurity)).

A solution of the borane.THF complex (123 ml, 123 mmol) was added slowly to a solution of Monomer Example 1 Stage 2 (103.64 g, 376 mmol) in dry tetrahydrofuran (1 L) and the mixture heated to 50° C. for 18 hrs. The reaction mixture was cooled to room temperature diglyme (1.3 L) was added, the mixture cooled to 0° C. and acetic acid (610 ml) was added dropwise, (effervescence was observed). The reaction mixture was stirred overnight at room temperature and then heated to 110° C., the tetrahydrofuran was distilled off and then the mixture was heated for a further 4 hrs at 110° C., after which it was cooled to room temperature and stirred overnight. Water (200 ml) was added to the reaction mixture, it was extracted with hexane (4×1 L), the combined organic extracts were washed with water (6×1 L), dried over MgSO$_4$ and the solvent removed under reduced pressure to give the title compound as a colourless oil. The oil was purified by a silica plug (eluting with hexane) to give the title compound as a colourless oil (92.87 g, 345 mmol, 93.9% pure by $^1$H NMR as a mixture of two isomers).

MS (EI) m/z 254 ((Br$^{81}$) M$^+$, 3%), 252 ((Br$^{79}$) M$^+$, 2), 57 (100).

$^1$H-NMR (600 MHz, CDCl$_3$): $\delta_H$ [ppm] 0.99 (s, 9H), 1.55 (dd, J=14.0 Hz, 8.8 Hz 1H), 1.75 (dd, J=14.0 Hz, 5.2 Hz, 1H), 2.78 (dd, J=14.2 Hz, 2.5 Hz, 1H), 3.36 (dd, J=14.2 Hz, 5.2 Hz, 1H), 3.47 (dtd, J=8.8 Hz, 5.2 Hz, 2.5 Hz, 1H), 6.93 (d, J=8.0 Hz, 1H), 7.19 (s, 1H), 7.32 (d, J=8.0 Hz, 1H), Monomer Example 1 Stage 3

To a solution of Monomer Example 1 Stage 2 (7.2 g, 26.4 mmol) in dry tetrahydrofuran (70 ml) at −78° C. under nitrogen, was added dropwise a solution of n-butyl lithium (2.5M in hexane, 11.0 ml, 27.5 mmol) so as to maintain an internal temperature of <−74° C. The reaction mixture was stirred for 20 minutes and an aliquot was quenched with water and analysed by GC-MS (BCBNp/BrBCBNp 80/20). BP methyl ester (4.35 g, 11.7 mmol) was added portion wise as a solid so as to keep the internal temperature <−74° C. The mixture was allowed to warm up slowly to room temperature over night; it was then cooled to 5° C. and quenched by the drop wise addition of HCl (2M aq). The solvent was removed under reduced pressure, the residue was extracted with hexane, the combined organic extracts were washed with water, dried over MgSO$_4$ and concentrated to dryness under reduced pressure. The crude Monomer Example 1 Stage 3 was taken onto the next step without any further purification.

Monomer Example 1

To a solution of Monomer Example 1 Stage 3 (9.19 g, 13.4 mmol) in dry dichloromethane (40 ml) at 0° C. under nitrogen, was added dropwise a solution of boron trifluoride diethyl etherate (8.23 ml, 66.9 mmol) so as to maintain an internal temperature of <5° C. The reaction mixture was allowed to warm up to room temperature, stirred over night and then poured carefully into a solution of ice:water (200 ml). Once the ice had melted, the phases were separated, the aqueous phase was extracted with dichloromethane and the combined organic extracts were stirred over an aqueous solution of potassium phosphate tribasic solution (10% wt:vol, 40 ml) for 30 minutes. The organic phase was separated and was washed with water (50 ml×3), dried over MgSO$_4$, filtered and adsorbed onto Isolute®. The dried Isolute® was loaded onto a silica/Florisil® plug and eluted with a mixture of hexane:dichloromethane (9:1 and 6:4) to give Monomer Example 1 as Frac 1 and Monomer Example 1 Stage 3 and Frac 2.

To a solution of Frac 2 (3.0 g, 4.3 mmol) in dry dichloromethane (12 ml) at 0° C. under nitrogen, was added dropwise a solution of boron trifluoride diethyl etherate (2.8 ml, 22.8 mmol) so as to maintain an internal temperature of <5° C. The reaction mixture was allowed to warm up to room temperature, stirred over night and then poured carefully into a solution of ice:water (50 ml). Once the ice had melted, phases were separated, the aqueous phase was extracted with dichloromethane and the combined organic extracts were stirred over an aqueous solution of potassium phosphate tribasic solution (10% wt:vol, 10 ml) for 30 minutes. The organic phase was separated and was washed with water (20 ml×3), dried over MgSO₄, filtered and adsorbed onto Isolute®. The dried Isolute® was loaded onto a silica/Florisil® plug and eluted with a mixture of hexane:dichloromethane (9:1). Fractions containing Monomer Example 1 were combined, reduced to dryness under reduced pressure and combined with Frac 1.

The resulting solid was recrystallised sequentially from n-butyl acetate:methanol followed by toluene:methanol to give Monomer Example 1 as a white solid (1.93 g, 22% yield, 100% pure by HPLC as a mixture of 2 isomers).

$^1$H-NMR (600 MHz, CDCl$_3$): δ$_H$ [ppm] 0.97 (s, 18H). 1.56 (dd, J=14.0 Hz, 8.7 Hz, 2H), 1.75 (dd, J=14.0 Hz, 5.3 Hz, 2H), 2.71 (dd, J=14.2 Hz, 2.3 Hz, 2H), 3.28 (dd, J=14.2 Hz, 5.2 Hz, 2H), 3.48 (m, 2H), 6.79 (s, 2H), 6.92 (d, J=7.8 Hz, 2H), 6.98 (dd, J=7.8 Hz, 0.96 Hz, 2H), 7.45 (dd, J=8.1 Hz, 1.6 Hz, 2H), 7.49 (d, J=1.3 Hz, 2H), 7.56 (d, J=8.1 Hz, 2H)

Monomer Example 2

Monomer Example 2 was prepared according to the following reaction scheme:

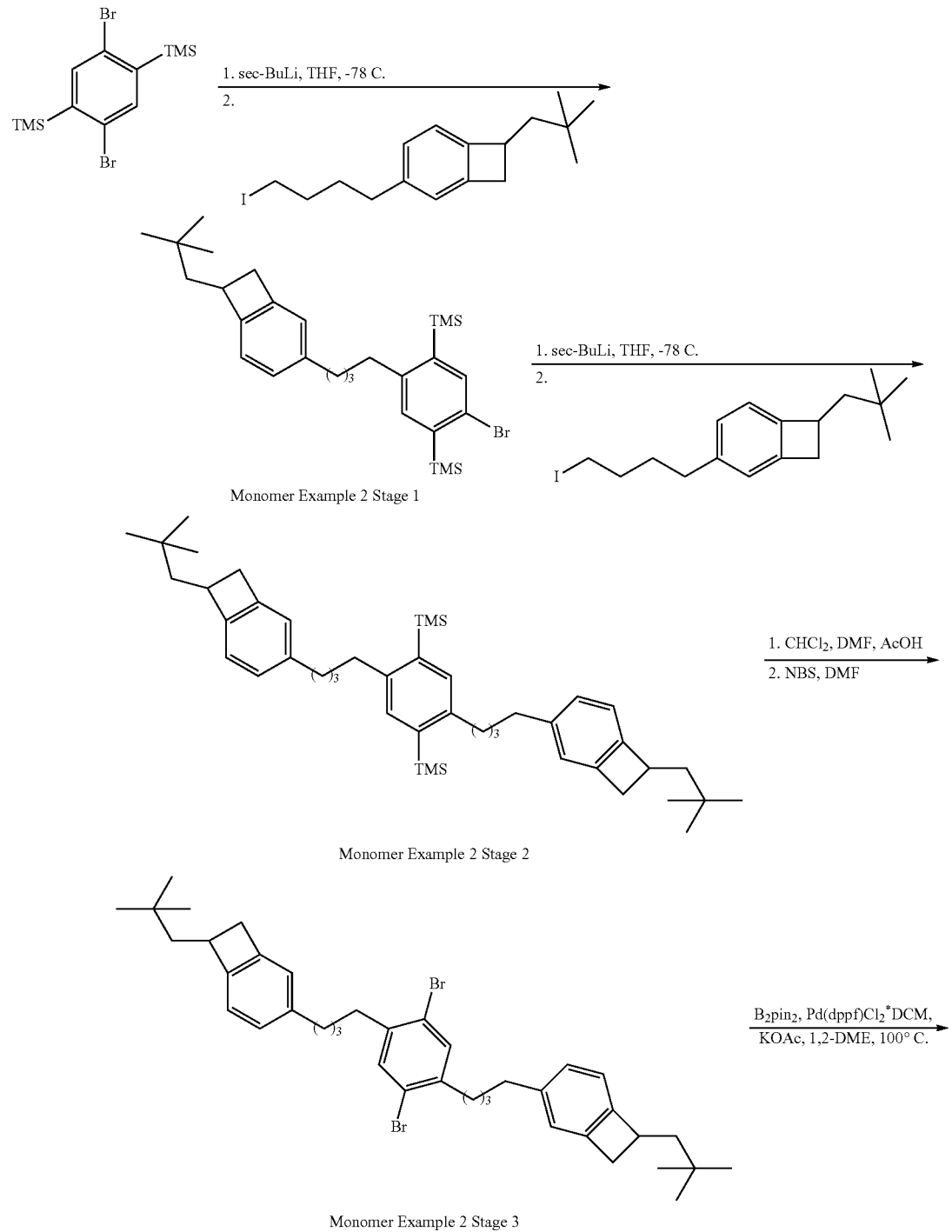

Monomer Example 2 Stage 1

Monomer Example 2 Stage 2

Monomer Example 2 Stage 3

-continued

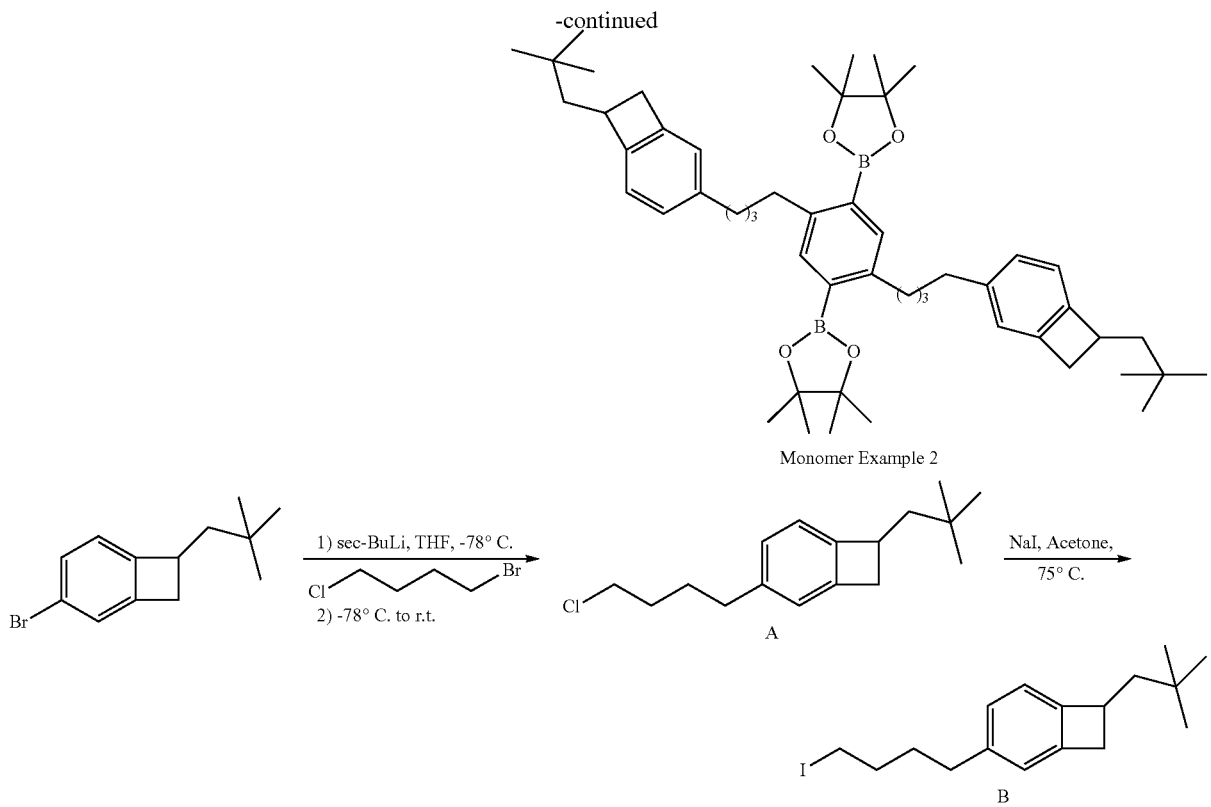

Monomer Example 2

3-(4-chlorobutyl)-7-neopentylbicyclo[4.2.0]octa-1,3,5-triene (A)

To a solution of 3-bromo-7-neopentylbicyclo[4.2.0]octa-1,3,5-triene (33.7 g, 123.8 mmol, 93% pure by GC-MS as mixture of 2 isomers) at −78° C. in dry THF (400 ml) at −78° C. under nitrogen, was added drop wise a solution of sec-butyl lithium (118 ml, 164.4 mmol, 1.4M in cyclohexane) so as to maintain an internal temperature of <−74° C. and the reaction mixture was stirred for a further 1 hr at −78° C. Then a solution of 1-bromo-4-chlorobutane (13.5 ml, 117.7 mmol) was added drop wise so as to maintain an internal temperature of <−74° C. and the mixture allowed to warm to room temperature over night. It was then cooled to 0° C., quenched by the drop wise addition of 2M HCl (100 ml) and concentrated under vacuum. The biphasic residue was extracted with hexane (3×120 ml), the combined organic extracts were washed with water (3×200 ml), dried (MgSO$_4$) and concentrated to dryness under vacuum. The resulting oil was purified using a silica plug (hexane, hexane: DCM 9:1) give 3-(4-chlorobutyl)-7-neopentylbicyclo[4.2.0]octa-1,3,5-triene as a colourless oil (28 g, 87% yield).

$^1$H-NMR (600 MHz, CDCl$_3$): δ$_H$ [ppm] 1.0 (s, 9H), 1.57 (dd, J=8.6 Hz, 13.9 Hz, 1H), 1.72-1.84 (m, 5H), 2.61 (t, J=7.6 Hz, 2H), 2.75 (dd, J=2.5 Hz, 13.9 Hz, 1H), 3.34 (dd, J=5.3 Hz, 13.9 Hz, 1H), 3.50 (m, 1H), 3.55 (t, J=6.5 Hz, 2H), 6.88 (s, 1H), 6.98 (m, 2H).

3-(4-iodobutyl)-7-neopentylbicyclo[4.2.0]octa-1,3,5-triene (B)

A mixture of 3-(4-chlorobutyl)-7-neopentylbicyclo[4.2.0]octa-1,3,5-triene (28.0 g, 105.7 mmol) and sodium iodide (79.2 g, 528.6 mmol) in acetone (300 ml) was refluxed for 25 hrs. The mixture was cooled to room temperature, water (250 ml) added and the mixture concentrated under vacuum. The biphasic residue was extracted with hexane (3×110 ml), the combined organic extracts were washed with water (5×100 ml), dried (MgSO$_4$) and concentrated under vacuum to yield 3-(4-iodobutyl)-7-neopentylbicyclo[4.2.0]octa-1,3,5-triene as a colourless oil (36.3 g, 96% yield, 95.8% HPLC purity as a mixture of 2 isomers).

$^1$H-NMR (600 MHz, CDCl$_3$): δ$_H$ [ppm] 1.0 (s, 9H), 1.57 (dd, J=8.6 Hz, 13.9 Hz, 1H), 1.71 (quint, 2H), 1.77 (dd, J=5.2 Hz, 13.9 Hz, 1H), 1.86 (quint, 2H), 2.60 (t, J=7.6 Hz, 2H), 2.75 (dd, J=2.3 Hz, 13.9 Hz, 1H), 3.20 (t, J=7.0 Hz, 2H), 3.34 (dd, J=5.2 Hz, 13.9 Hz, 1H), 3.50 (m, 1H), 6.88 (s, 1H), 6.98 (m, 2H).

Monomer Example 2 Stage 1

To a solution of 1,4-dibromo-3,6-(trimethylsilyl) benzene (20.0 g, 52.6 mmol) in dry THF (200 ml) at −78° C. under nitrogen, was added drop wise a solution of sec-butyl lithium 47.8 ml, 68.4 mmol, 1.4M in cyclohexane) so as to maintain an internal temperature of <−74° C. The reaction mixture was stirred for a further 1 hr at −78° C. Then a solution of 3-(4-iodobutyl)-7-neopentylbicyclo[4.2.0]octa-1,3,5-triene (19.7 g, 55.2 mmol) in THF (20 ml) was added drop wise while maintaining the internal temperature of <−74° C. and the mixture was allowed to warm to room temperature over night. It was then cooled to 0° C., quenched by the drop wise addition of 2M HCl (50 ml), concentrated under vacuum, and the biphasic residue was extracted with hexane (3×70 ml). The combined organic extracts were washed with water (3×100 ml), dried (MgSO$_4$) and concentrated under vacuum. The resulting oil was purified using a silica plug (hexane) yield Monomer Example 2 stage 1 as colourless oil (18.2 g, 65% yield, 85.8% HPLC purity as a mixture of 2 isomers).

$^1$H-NMR (600 MHz, CDCl$_3$): $\delta_H$ [ppm] 0.29 (s, 9H), 0.38 (s, 9H), 1.0 (s, 9H), 1.53-16.3 (m, 3H), 1.71 (quint, 2H), 1.76 (dd, J=5.3 Hz, 13.9 Hz, 1H), 2.63 (m, 4H), 2.74 (dd, J=2.3 Hz, 13.9 Hz, 1H), 3.33 (dd, J=5.2 Hz, 13.9 Hz, 1H), 3.50 (m, 1H), 6.89 (s, 1H), 6.96 (d, J=7.5 Hz, 1H), 7.00 (d, J=7.5 Hz, 1H), 7.20 (s, 1H), 7.35 (s, 1H).

Monomer Example 2 Stage 2

To a solution of Monomer B stage 1 (18.2 g, 34.4 mmol) in dry THF (200 ml) at −78° C. under nitrogen, was added drop wise a solution of sec-butyl lithium (29.4 ml, 41.2 mmol, 1.4M in cyclohexane) so as to maintain an internal temperature of <−74° C. and the reaction mixture was stirred for a further 1 hr at −78° C. Then a solution of 3-(4-iodobutyl)-7-neopentylbicyclo[4.2.0]octa-1,3,5-triene (12.9 g, 36.1 mmol) in THF (20 ml) was added drop wise while maintaining the internal temperature of <−74° C. and the mixture was allowed to warm to room temperature over night. It was then cooled to 0° C., quenched by the drop wise addition of 2M HCl (25 ml), concentrated under vacuum and diluted with toluene (100 ml). The phases were separated and the aqueous layer was diluted with water (50 ml) and extracted with toluene (2×50 ml). The combined organic extracts were washed with water (3×100 ml), dried (MgSO$_4$) and concentrated under vacuum. The resulting solid was stirred in acetonitrile (250 ml) for 3 hrs, filtered and dried in a vacuum oven at 40° C. for 68 hrs to yield Monomer Example 2 stage 2 as white solid (17.8 g, 76% yield, 95.5% HPLC purity).

$^1$H-NMR (600 MHz, CDCl$_3$): $\delta_H$ [ppm] 0.28 (s, 18H), 1.0 (s, 18H), 1.56 (dd, J=8.7 Hz, 13.9 Hz, 2H), 1.63 (m, 4H), 1.72 (m, 4H), 1.76 (dd, J=5.3 Hz, 13.9 Hz, 2H), 2.63 (t, J=7.5 Hz, 4H), 2.67 (m, 4H), 2.75 (dd, J=2.0 Hz, 13.9 Hz, 2H), 3.33 (dd, J=5.2 Hz, 13.9 Hz, 2H), 3.49 (m, 2H), 6.89 (s, 2H), 6.96 (d, J=7.5 Hz, 2H), 7.00 (d, J=7.5 Hz, 2H), 7.35 (s, 2H).

Monomer Example 2 Stage 3

To a solution of Monomer B stage 2 (17.8 g, 26.2 mmol) in chloroform (180 ml) at 5° C. under nitrogen, shielded from light, was added drop wise acetic acid (32 ml) followed by DMF (71 ml) so as to maintain the temperature <10° C. The mixture was allowed to warm to room temperature and purged with nitrogen for 30 mins. A solution of N-bromosuccinimide (9.6 g, 53.7 mmol) in DMF (33 ml) which had been purged with nitrogen for 30 mins was added drop wise at 5° C. to the solution of Monomer B Stage 2 and the resulting mixture was allowed to warm up to room temperature and stirred for a further 3 hrs. A further portion of N-bromosuccinimide (0.4 g, 2.25 mmol) was added as a solid at 5° C. and the reaction stirred at room temperature over night. The mixture was cooled down to 10° C., water (170 ml) was added to the reaction mixture, the phases were separated, the aqueous layer was extracted with DCM (2×100 ml), the combined organic extracts were washed with water (5×100 ml) dried (MgSO$_4$) and concentrated under vacuum. The resulting solid was stirred in acetonitrile (250 ml) for 3 hrs, filtered and dried in a vacuum oven at 50° C. for 18 hours to yield Monomer Example 2 stage 3 as white solid (16.7 g, 92% yield, 95.6% pure by HPLC).

$^1$H-NMR (600 MHz, CDCl$_3$): $\delta_H$ [ppm] 0.99 (s, 18H), 1.57 (dd, J=8.6 Hz, 13.9 Hz, 2H), 1.65 (m, 8H), 1.77 (dd, J=5.3 Hz, 13.9 Hz, 2H), 2.61 (t, J=7.4 Hz, 4H), 2.67 (t, J=7.4 Hz, 4H), 2.75 (dd, J=2.3 Hz, 13.9 Hz, 2H), 3.34 (dd, J=5.2 Hz, 13.9 Hz, 2H), 3.50 (m, 2H), 6.88 (s, 2H), 6.96 (d, J=7.4 Hz, 2H), 7.00 (d, J=7.5 Hz, 2H), 7.33 (s, 2H).

Monomer Example 2

A solution of Monomer Example 2 stage 3 (16.7 g, 24.1 mmol) and bis(pinacolato)diboron (13.5 g, 53.0 mmol) in 1,2-dimethoxy ethane (200 ml) was purged with nitrogen for 1 hr, potassium acetate (14.2 g, 144.7 mmol) was added the mixture purged for a further 20 mins. 1,1′-Bis(diphenylphosphino) ferrocene palladium dichloride dichloromethane adduct (0.59 g, 0.72 mmol) was added and the mixture stirred at 100° C. over night. The mixture was cooled down to room temperature, filtered through a silica-Florisil-celite plug (DCM:hexane (1:1)) and concentrated under vacuum. The resulting residue was dissolved in DCM and hexane was added and the DCM was removed under vacuum to obtain a mixture of DCM:hexane (1:1). The solution was filtered through a silica-Forisil plug (DCM:hexane (1:1)), and concentrated to dryness under educed pressure. The resulting solid was recrystallised repeatedly from toluene: acetonitrile, toluene:hexane and toluene:acetonitrile:isopropanol and then purified by column chromatography (hexane:DCM (7:3) to (6:4)) and the resulting solid was dissolved in toluene, acetonitrile was added to the mixture and the resulting slurry was filtered to give Monomer Example 2 as white solid (9.6 g, 50% yield, 99.8% pure by HPLC).

$^1$H-NMR (600 MHz, CDCl$_3$): $\delta_H$ [ppm] 0.99 (s, 18H), 1.31 (s, 24H), 1.58 (m, 6H), 1.66 (quint, 4H), 1.76 (dd, J=5.3 Hz, 13.9 Hz, 2H), 2.59 (t, J=7.7 Hz, 4H), 2.74 (dd, J=2.0 Hz, 13.9 Hz, 2H), 2.84 (t, J=7.9 Hz, 4H), 3.32 (dd, J=5.2 Hz, 13.9 Hz, 2H), 3.48 (m, 2H), 6.87 (s, 2H), 6.94 (d, J=7.5 Hz, 2H), 6.99 (d, J=7.5 Hz, 2H), 7.53 (s, 2H).

Monomer C

Monomer C was prepared according to the following reaction scheme:

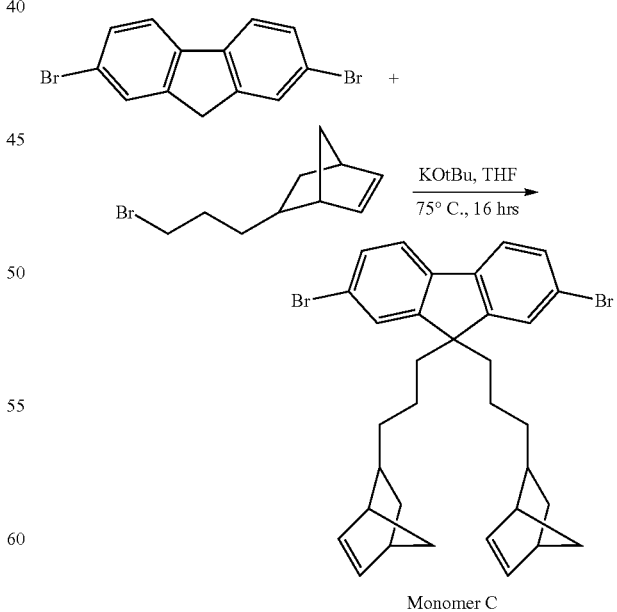

Monomer C

To a solution of 2,7-dibromo-9H-fluorene (2 g, 6.17 mmol) in dry THF (20 ml) under nitrogen, was added potassium tert-butoxide (3.4 g, 30.86 mol) and the mixture stirred at 70° C. for 2 hrs. The reaction mixture was cooled to room temperature, 5-(3-bromoprop-1-yl)-bicyclo[2.2.1]hept-2-ene (3.9 g, 18.52 mol) in dry THF (5 ml) was added drop wise and then the mixture was stirred at 75° C. for 16 hrs. On cooling, water (50 ml) was added and the solution extracted with dichloromethane (2×50 ml). The combined organic extracts were washed with water (50 ml), brine (50 ml), dried ($Na_2SO_4$) and concentrated under reduced pressure to give an yellow solid. Purification by silica gel column chromatography (hexane) gave a solid which was triturated with a mixture of MeOH/EtOAc (5 ml:3 ml) at 50° C. for 30 mins. The solid was filtered and washed with methanol to give Monomer C as a white solid (1.16 g, 32% yield, 99.8% purity by HPLC).

$^1$H-NMR (400 MHz, $CDCl_3$): $\delta_H$ [ppm] 0.26-0.30 (m, 2H), 0.57-0.63 (m, 4H), 0.82-0.87 (m, 4H), 1.09-1.19 (m, 2H), 1.27-1.29 (m, 2H), 1.64-1.69 (m, 2H), 1.71-1.76 (m, 2H), 1.86-1.92 (m, 4H), 2.50 (m, 2H,), 2.66 (m, 2H), 5.72 (dd, J=2.8 Hz, 5.6 Hz, 2H), 6.03 (dd, J=2.9 Hz, 5.6 Hz, 2H), 7.45-7.49 (m, 4H), 7.54-7.56 (m, 2H).

Polymer Examples

Polymers were prepared by Suzuki polymerisation as described in WO 00/53656 of monomers illustrated below in the amounts set out in Table 1.

TABLE 1

| Polymer | Diester monomers (mol %) | Dibromo monomers (mol %) |
| --- | --- | --- |
| Comparative Polymer 1 | A (50) | Comparative Monomer 1 (5) D (40), B (5) |
| Polymer Example 1 | A (50) | Monomer Example 1 (5) D (40), B (5) |
| Polymer Example 2 | A (50) | Monomer Example 1 (5) D (40), C (5) |
| Polymer Example 3 | A (45) Monomer Example 2 (5) | D (40), E (5), C (5) |
| Comparative Polymer 3 | A (45) Comparative Monomer 2 (5) | D (40), E (5), C (5) |
| Polymer Example 4 | A (45), F (5) | D (40) E (5), Monomer Example 1 (5) |

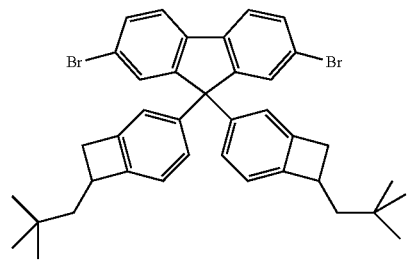

Monomer Example 1

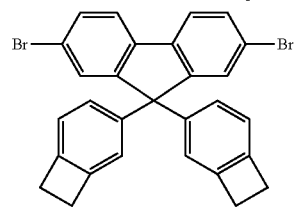

Comparative Monomer 1

TABLE 1-continued

| Polymer | Diester monomers (mol %) | Dibromo monomers (mol %) |
| --- | --- | --- |

Monomer Example 2

Comparative Monomer 2

Monomer A

Monomer B

Monomer C

Monomer D

TABLE 1-continued

| Polymer | Diester monomers (mol %) | Dibromo monomers (mol %) |
|---|---|---|

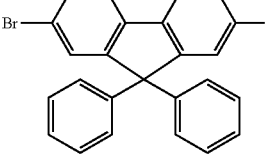

Monomer E

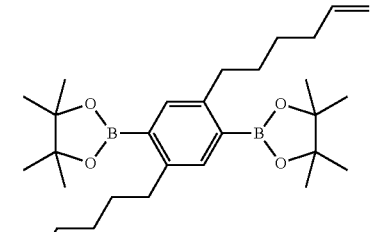

Monomer F

Non-Polymeric Compound Reaction Example 1

30-40 mg of Compound Example 1 was weighed out into a glass disc. The glass disc was heated in a glovebox ($O_2$<0.1 ppm) and the mixture was stirred for 1 hr with a magnetic stirrer bar.

The resultant mixture was dissolved and analysed by HPLC and LC-MS, in which the peaks corresponding to the starting material were normalised to 100%.

Non-Polymeric Compound Reaction Comparative Example 1

A reaction was performed as described in Example 1 except that Comparative Compound 1, illustrated below, was used in place of Compound Example 1.

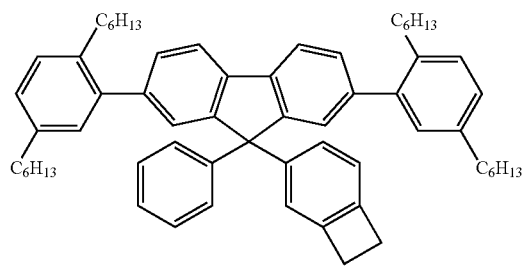

Comparative Compound 1

Non-Polymeric Compound Reaction Comparative Example 2

A reaction was performed as described in Example 1 except that Comparative Compound 2, illustrated below, was used in place of Compound Example 1.

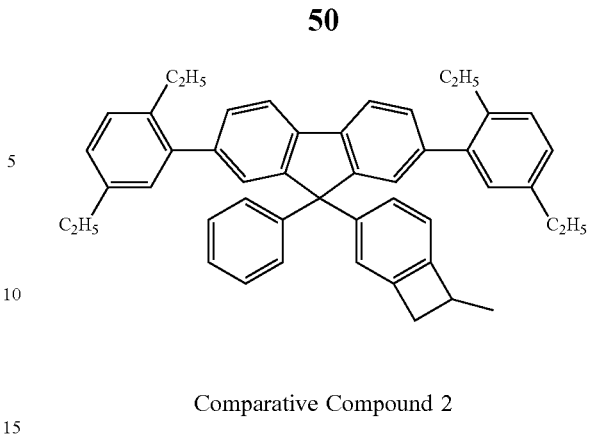

Comparative Compound 2

Figure 2A:
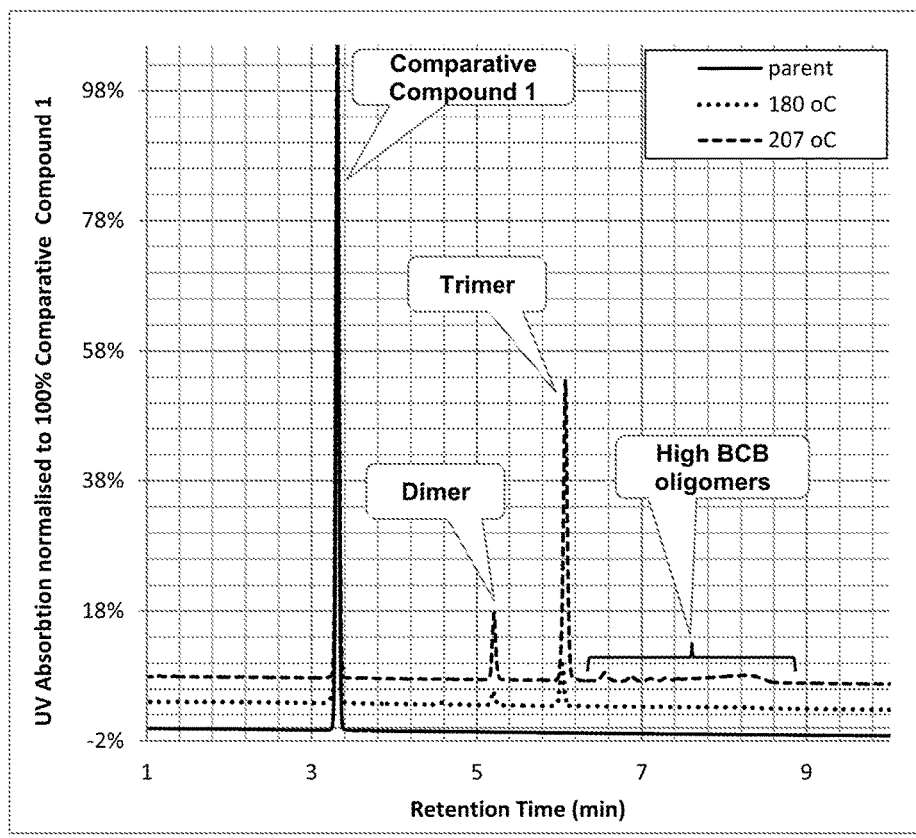
FIG. 2A shows the HPLC trace of a product mixture obtained by reaction of a comparative compound containing unsubstituted BCB.
Figure 2B:
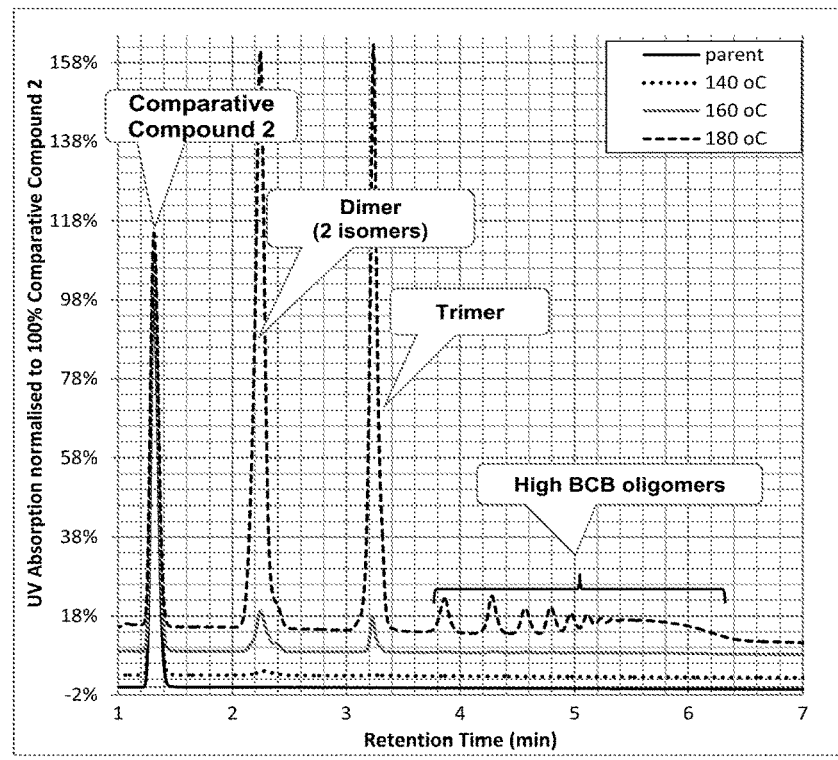
FIG. 2B shows the HPLC trace of a product mixture obtained by reaction of a comparative compound containing methyl-substituted BCB.
Figure 2C:
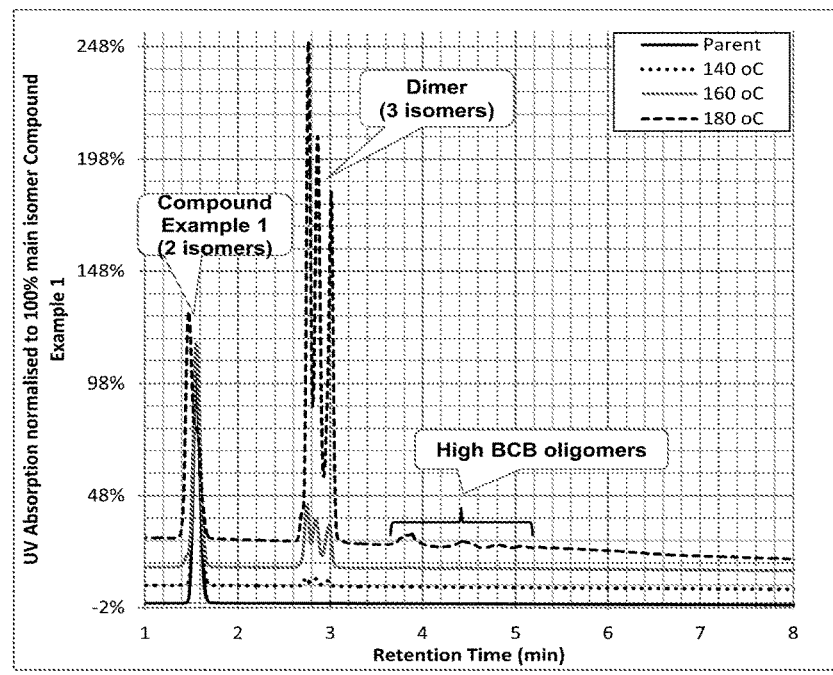
FIG. 2C shows the HPLC trace of a product mixture obtained by reaction of a compound according to an embodiment of the invention containing neopentyl-substituted BCB.

With reference to FIGS. 2A-2C, Comparative Compounds 1 and 2 (FIGS. 2A and 2B respectively) react to form substantial amounts of trimers and higher oligomers, whereas the product of the reaction of Compound Example 1 (FIG. 2C) is dominated by dimer formation with little trimer or higher oligomer formation. Without wishing to be bound by any theory, it is believed that the bulky neopentyl substituent of Compound Example 1 inhibits formation of trimers or higher oligomers, increasing favourability of reaction with a group of formula (II), if present.

Polymer Reaction Examples

A 35 nm hole injection layer was formed by spin-coating a hole-injection material available from Nissan Chemical Industries on a glass substrate and annealed A 22 nm layer of a polymer of Table 1 above was formed by spin-coating on the hole-injection layer and heated to a temperature between 120 C and 230 C for 1 hour.

The polymer layer was then soaked in ortho-xylene solvent for 5 minutes.

The quantity of polymer that dissolved upon soaking was determined by comparing UV-vis absorption spectra at 376 nm before and after soaking in ortho xylene.

Figure 3:
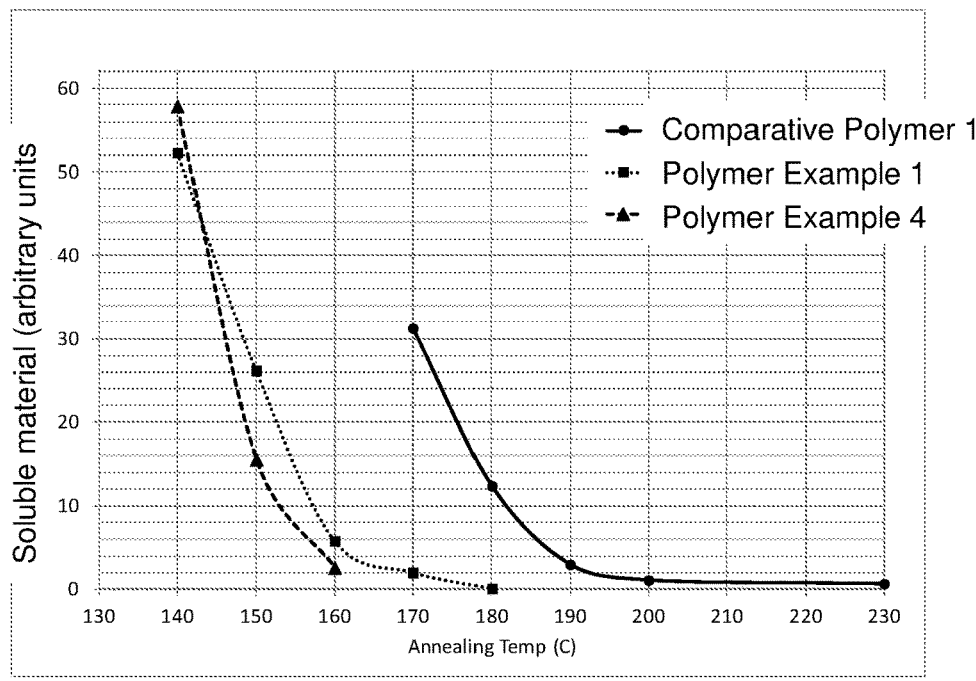
FIG. 3 is a graph of soluble material removed after heating vs. heating temperature for polymers according to embodiments of the invention and comparative polymers.

With reference to FIG. 3, crosslinking of Polymer Example 1 and 4, which contain a neopentyl-substituted BCB, results in significantly less soluble material than crosslinking of Comparative Polymer 1 which contains an unsubstituted BCB group.

Device Examples—Spin-Coated Hole-Transporting Layer

A blue organic light-emitting device having the following structure was prepared:
ITO/HIL (35 nm)/HTL (22 nm)/LE (65 nm)/Cathode,
wherein ITO is an indium-tin oxide anode; HIL is a hole-injecting layer; HTL is a hole-transporting layer; LE is a light-emitting layer; and the cathode comprises a layer of sodium fluoride in contact with the light-emitting layer, a layer of aluminium and a layer of silver.

To form the device, a substrate carrying ITO was cleaned using UV/Ozone. The hole injection layer was formed by spin-coating an aqueous formulation of a hole-injection material available from Nissan Chemical Industries and heating the resultant layer. The hole transporting layer was formed by spin-coating a polymer of Table 1 and crosslinking the polymer by heating. The light-emitting layer was formed by spin-coating composition of a blue light-emitting polymer comprising repeat units of formulae (VII), (VIII) and (X). The cathode was formed by evaporation of a first layer of sodium fluoride to a thickness of about 2 nm, a second layer of aluminium to a thickness of about 100 nm and a third layer of silver to a thickness of about 100 nm.

The hole-transporting layers were annealed at 160° C. for 1 hour, except for Comparative Polymer 1 which was annealed at 170° C. for 1 hour.

Figure 4:
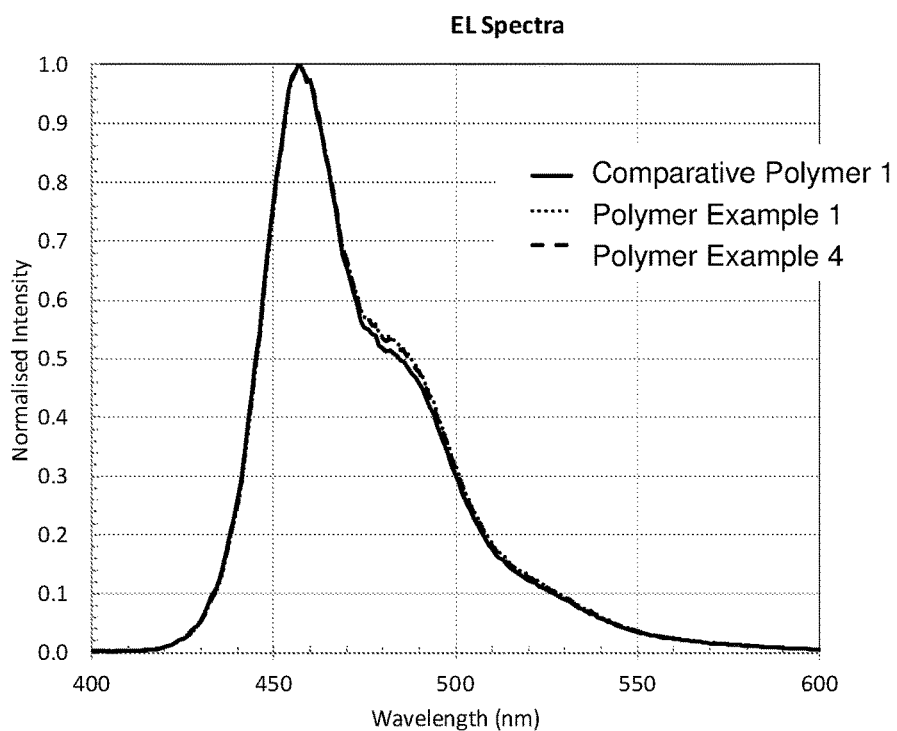
FIG. 4 shows the electroluminescence spectra for devices according to embodiments of the invention and comparative devices.

With reference to FIG. 4, the spectra using different hole-transporting layers are very similar.

Figure 5:
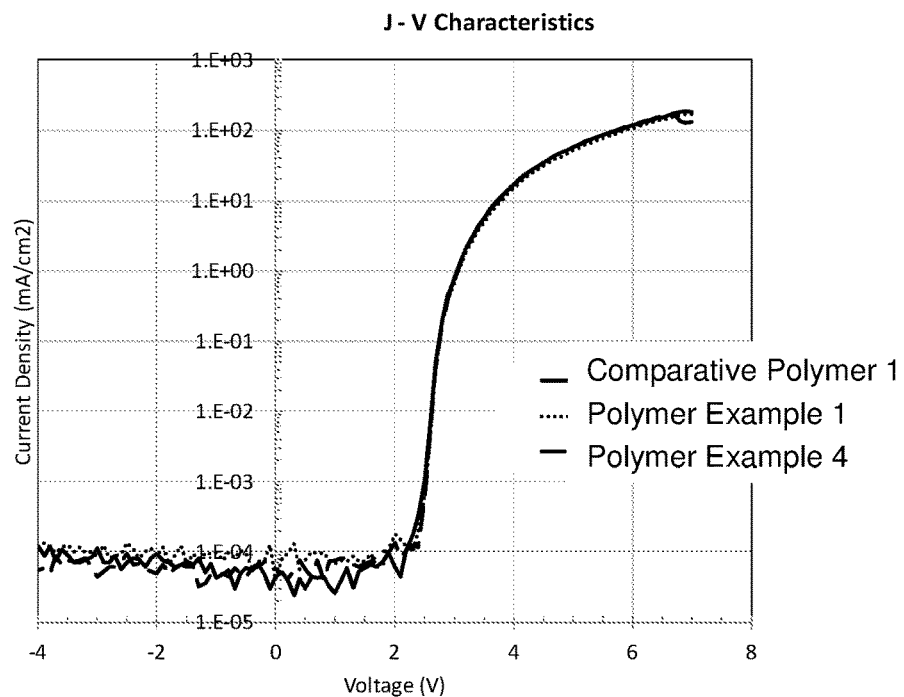
FIG. 5 shows graphs of current density vs. voltage for devices according to embodiments of the invention and comparative devices.

With reference to FIG. 5, current density at a given voltage is similar for the different devices. The voltage required to achieve a current density of 10 mA/cm$^2$ was 3.7 V in all cases.

Figure 6:
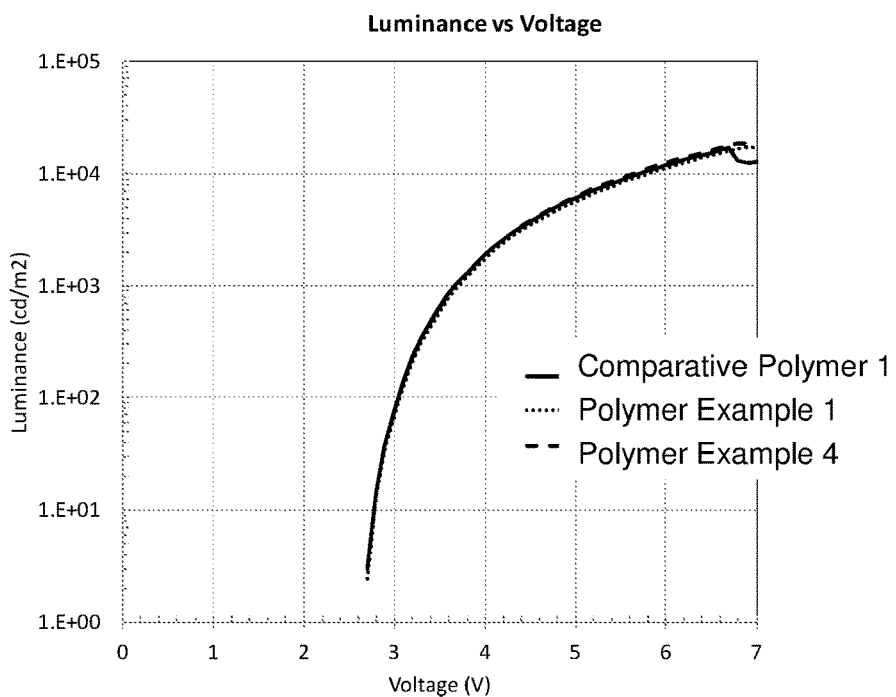
FIG. 6 shows luminance vs. voltage graphs for devices according to embodiments of the invention and comparative devices.

With reference to FIG. 6, luminance vs. voltage traces for the devices are very similar. The voltage required to achieve a brightness of 1000 cd/m$^2$ was 3.7 V in all cases.

Figure 7:
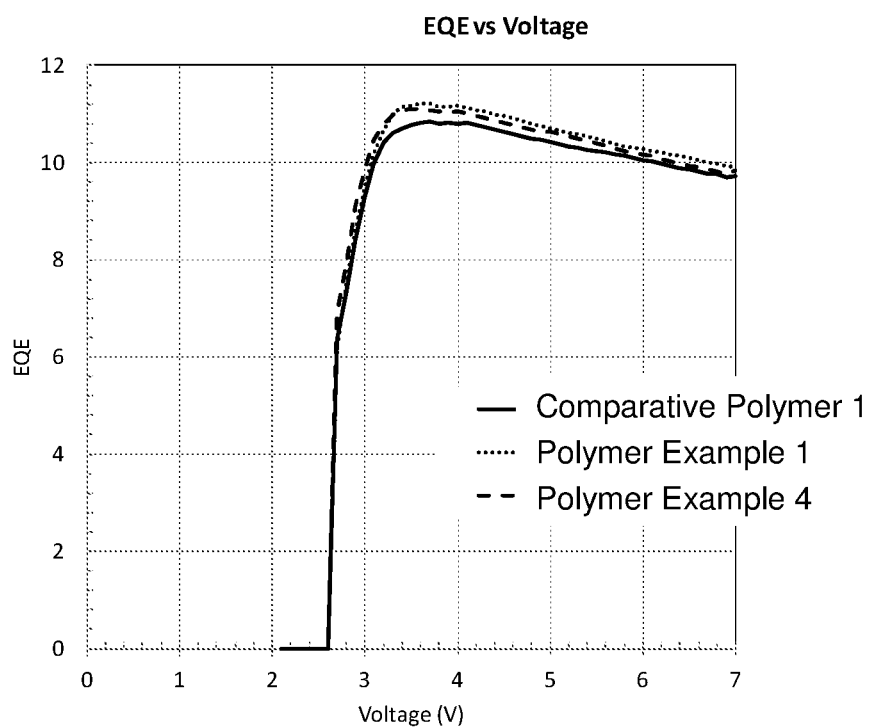
FIG. 7, shows external quantum efficiency vs. voltage graphs for devices according to embodiments of the invention and comparative devices.

With reference to FIG. 7, the external quantum efficiencies of devices containing Polymer Examples 1 and 4 are higher than that of a device containing Comparative Polymer 1.

Device Examples—Inkjet Printed Hole-Transporting Layer

A blue organic light-emitting device having the following structure was prepared:
ITO/HIL (35 nm)/HTL (22 nm)/LE (65 nm)/Cathode,
wherein ITO is an indium-tin oxide anode; HIL is a hole-injecting layer; HTL is a hole-transporting layer; LE is a light-emitting layer; and the cathode comprises a layer of sodium fluoride in contact with the light-emitting layer and a layer of aluminium.

To form the device, a substrate carrying ITO was cleaned using UV/Ozone. A photoresist layer was formed on the ITO and patterned to form inkjet wells. The hole injection layer was formed by inkjet printing an aqueous formulation of a hole-injection material available from Nissan Chemical Industries into the wells and heating the resultant layer. The hole transporting layer was formed by inkjet printing a polymer comprising fluorene repeat units of formula (VIIa), amine repeat units of formula (X-1), and 5 mol % each of repeat units derived from Comparative Monomer 1 and Monomer B dissolved in an 80:20 vol % blend of cyclohexylbenzene:4-methylanisole into the wells and crosslinking the polymer by heating at 170° C. for 1 hour. The light-emitting layer was formed by inkjet printing a formulation comprising a light-emitting polymer comprising repeat units of formulae (VIIa), (VIII) and (X) dissolved in an 80:20 vol % blend of cyclohexylbenzene:4-methylanisole. The cathode was formed by evaporation of a first layer of sodium fluoride to a thickness of about 2 nm and a second layer of aluminium to a thickness of about 100 nm.

A device was formed by inkjet printing as described above except that the hole-transporting layer was rinsed with solvent prior to formation of the light-emitting layer.

Figure 8:
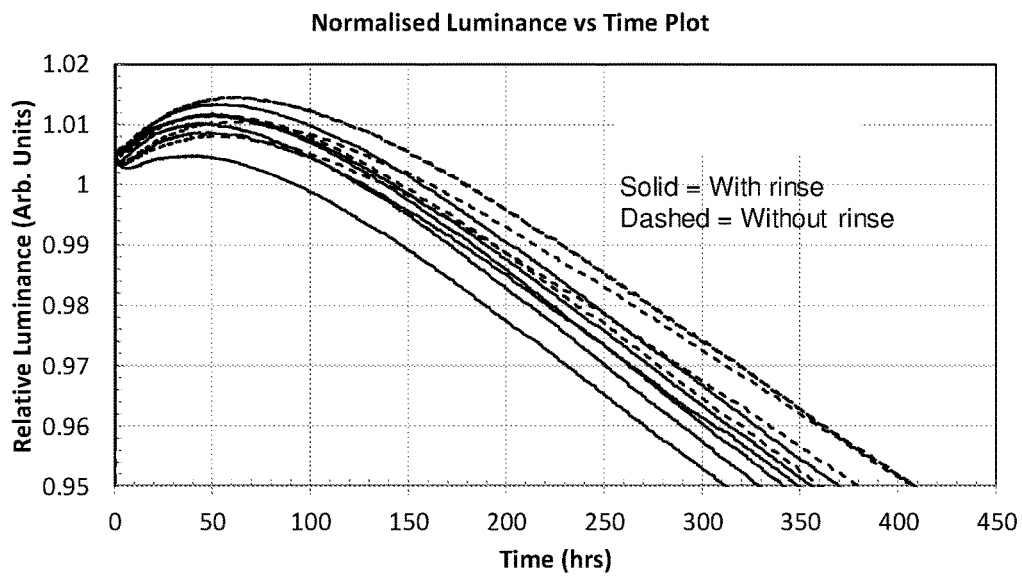
FIG. 8 is a graph of luminance vs. time for inkjet printed OLEDs according to embodiments of the invention.

With reference to FIG. 8, the time taken for luminance to fall to 95% of an initial value is similar for the devices with rinsing (solid line) and without rinsing (dashed line) of the hole-transporting layer.

For the purpose of comparison, two comparative devices were formed by inkjet printing as described above, wherein the hole-transporting layer of one device was rinsed with solvent prior to formation of the light-emitting layer and the other was not so rinsed, except that the repeat unit derived from Comparative Monomer 1 was used in place of repeat units derived from Monomer Example 1. The hole-transporting polymer of the comparative devices was deposited by inkjet printing a formulation of the polymer dissolved in a 50:50 vol % blend of anisole:3-phenoxytoluene.

Figure 9:
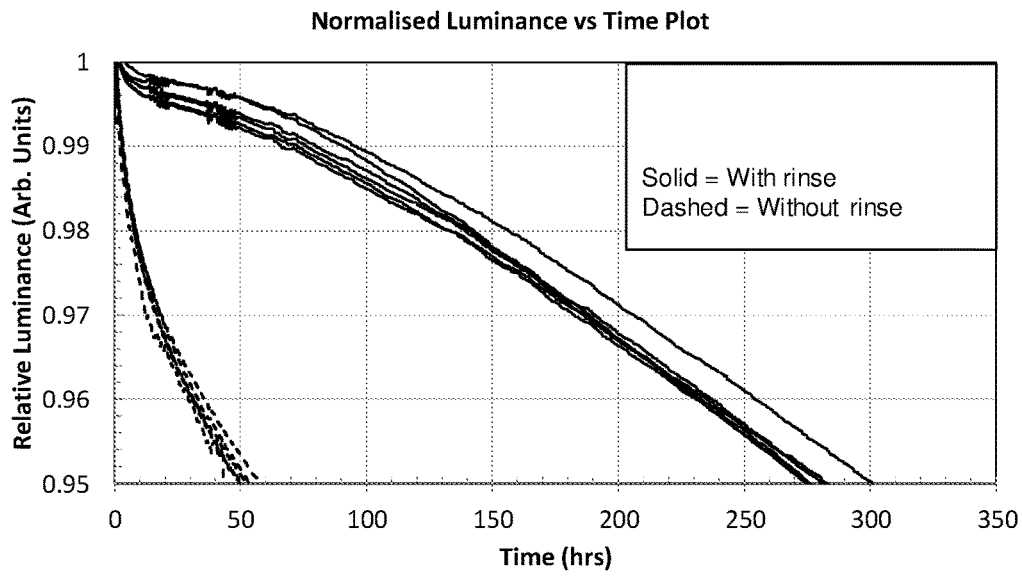
FIG. 9 is a graph of luminance vs. time for comparative inkjet printed OLEDs.

With reference to FIG. 9, the time taken for luminance to fall to 95% of an initial value is much longer for the comparative device having a rinsed hole-transporting layer (solid line) than the comparative device formed without rinsing the hole-transporting layer (dashed line). Without wishing to be bound by any theory, it is believed that the relatively short lifetime of the device containing an unrinsed hole-transporting layer is at least in part due to the presence of uncrosslinked hole-transporting polymer that is removed in the rinsed device.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A material, wherein the material is a polymer comprising a first repeat unit of formula (IIIb):

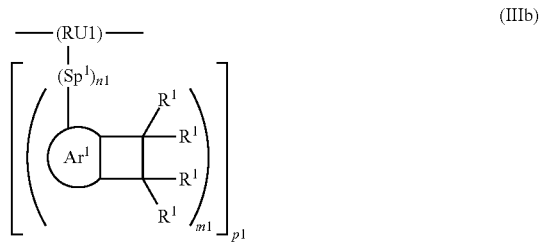

wherein:
RU1 is a first polymer backbone repeating group;
p1 is at least 1;
Ar$^1$ is an aryl or heteroaryl group that may be unsubstituted or substituted with one or more substituents;
Sp$^1$ represents a first spacer group;
n1 is 0 or 1;
m1 is 1 if n1 is 0 and m1 is at least 1 if n1 is 1; and
R$^1$ independently in each occurrence is H or a substituent, with the proviso that at least one R$^1$ is a group R$^{11}$ selected from:
   alkyl comprising a tertiary carbon atom directly bound to a carbon atom of the cyclobutene ring of formula (I);
   branched alkyl wherein a secondary or tertiary carbon atom of the branched alkyl is spaced from a carbon atom of the cyclobutene ring of formula (I) by at least one —CH$_2$— group; and
   alkyl comprising a cyclic alkyl group;
or
with the proviso that at least two R$^1$ groups are linked to form a ring.

2. The material according to claim 1 wherein RU1 is an unsubstituted or substituted arylene group.

3. A composition comprising a material substituted with a group of formula (I):

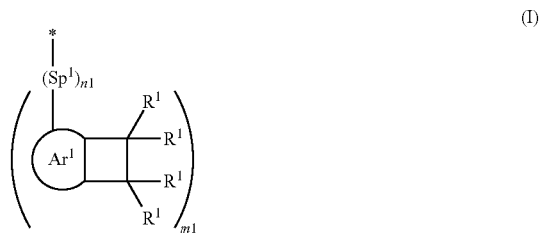

wherein:
Ar$^1$ is an aryl or heteroaryl group that may be unsubstituted or substituted with one or more substituents;

Sp¹ represents a first spacer group;
n1 is 0 or 1;
m1 is 1 if n1 is 0 and m1 is at least 1 if n1 is 1;
R¹ independently in each occurrence is H or a substituent, with the proviso that at least one R¹ is a group R¹¹ selected from:
  alkyl comprising a tertiary carbon atom directly bound to a carbon atom of the cyclobutene ring of formula (I);
  branched alkyl wherein a secondary or tertiary carbon atom of the branched alkyl is spaced from a carbon atom of the cyclobutene ring of formula (I) by at least one —CH₂— group; and
  alkyl comprising a cyclic alkyl group;
or
with the proviso that at least two R¹ groups are linked to form a ring;
and * represents a point of attachment to the material;
and a second material substituted with at least one group of formula (II):

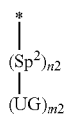
(II)

wherein
Sp² represents a second spacer group;
n2 is 0 or 1;
m2 is 1 if n2 is 0 and m2 is at least 1 if n2 is 1;
UG is a group comprising a reactive unsaturated group; and
* represents a point of attachment to the second material.

4. The composition according to claim 3 wherein the group of formula (II) independently in each occurrence is selected from groups of formula (XIa) and (XIb):

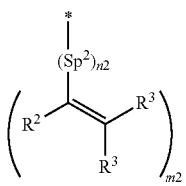
(XIa)

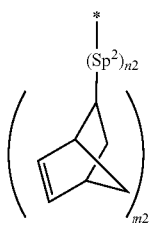
(XIb)

wherein R² and R³ each independently represent H or a substituent and wherein the norbornene group of formula (XIb) may be unsubstituted or substituted with one or more substituents.

5. The composition according to claim 3 wherein the second material is a polymeric repeat unit of formula (IVb):

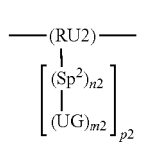
(IVb)

wherein RU2 is a second repeat unit and p2 is at least 1.

6. The composition according to claim 3 wherein the material and the second material are repeat units of the same polymer.

7. The composition according to claim 3 wherein the second material is a non-polymeric compound.

8. A method of forming a layer of an organic electronic device comprising the step of depositing and reacting a material substituted with a group of formula (I):

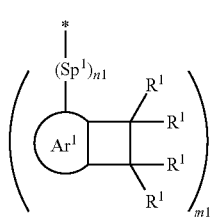
(I)

wherein:
Ar¹ is an aryl or heteroaryl group that may be unsubstituted or substituted with one or more substituents;
Sp¹ represents a first spacer group;
n1 is 0 or 1;
m1 is 1 if n1 is 0 and m1 is at least 1 if n1 is 1;
R¹ independently in each occurrence is H or a substituent, with the proviso that at least one R¹ is a group R¹¹ selected from:
  alkyl comprising a tertiary carbon atom directly bound to a carbon atom of the cyclobutene ring of formula (I);
  branched alkyl wherein a secondary or tertiary carbon atom of the branched alkyl is spaced from a carbon atom of the cyclobutene ring of formula (I) by at least one —CH₂— group; and
  alkyl comprising a cyclic alkyl group;
or
with the proviso that at least two R¹ groups are linked to form a ring;
and * represents a point of attachment to the material or a composition comprising a material substituted with a group of formula (I):

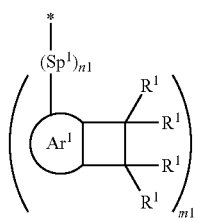
(I)

wherein:
Ar¹ is an aryl or heteroaryl group that may be unsubstituted or substituted with one or more substituents;
Sp¹ represents a first spacer group;

n1 is 0 or 1;
m1 is 1 if n1 is 0 and m1 is at least 1 if n1 is 1;
$R^1$ independently in each occurrence is H or a substituent, with the proviso that at least one $R^1$ is a group $R^{11}$ selected from:
  alkyl comprising a tertiary carbon atom directly bound to a carbon atom of the cyclobutene ring of formula (I);
  branched alkyl wherein a secondary or tertiary carbon atom of the branched alkyl is spaced from a carbon atom of the cyclobutene ring of formula (I) by at least one —CH$_2$— group; and
  alkyl comprising a cyclic alkyl group;
or
with the proviso that at least two $R^1$ groups are linked to form a ring;
and * represents a point of attachment to the material;
and a second material substituted with at least one group of formula (II):

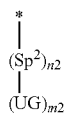
(II)

wherein
Sp$^2$ represents a second spacer group;
n2 is 0 or 1;
m2 is 1 if n2 is 0 and m2 is at least 1 if n2 is 1;
UG is a group comprising a reactive unsaturated group; and
* represents a point of attachment to the second material.

9. The method according to claim 8 wherein the reaction takes place at a temperature of less than 200° C.

10. The method according to claim 8 wherein the material or composition is deposited from a solution in a solvent or solvent mixture followed by evaporation of the solvent or solvents.

11. The method according to claim 10 wherein the material or composition is inkjet printed.

12. The method according to claim 8 wherein a further layer is formed by a solution deposition method on the layer comprising the reacted material or composition.

13. The method according to claim 12 wherein the further layer is formed by inkjet printing.

14. The method according to claim 8 wherein the organic electronic device is an organic light-emitting device.

15. The method according to claim 14 wherein the layer is a hole transporting layer provided between an anode and a light-emitting layer of the organic light-emitting device.

* * * * *